(12) United States Patent
McDermott et al.

(10) Patent No.: US 12,251,544 B2
(45) Date of Patent: Mar. 18, 2025

(54) SYSTEM AND METHOD FOR AIR DETECTION IN FLUID INJECTOR

(71) Applicant: BAYER HEALTHCARE LLC, Whippany, NJ (US)

(72) Inventors: Michael McDermott, Pittsburgh, PA (US); William Barone, Pittsburgh, PA (US); Barry Iddon, Jeannette, PA (US); John Volkar, Valencia, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1164 days.

(21) Appl. No.: 17/048,219

(22) PCT Filed: Apr. 18, 2019

(86) PCT No.: PCT/US2019/028124
§ 371 (c)(1),
(2) Date: Oct. 16, 2020

(87) PCT Pub. No.: WO2019/204605
PCT Pub. Date: Oct. 24, 2019

(65) Prior Publication Data
US 2021/0146063 A1    May 20, 2021

Related U.S. Application Data

(60) Provisional application No. 62/723,711, filed on Aug. 28, 2018, provisional application No. 62/659,988, filed on Apr. 19, 2018.

(51) Int. Cl.
*A61M 5/36*     (2006.01)
*A61M 5/00*     (2006.01)
(Continued)

(52) U.S. Cl.
CPC ............ *A61M 5/365* (2013.01); *A61M 5/007* (2013.01); *A61M 5/3146* (2013.01);
(Continued)

(58) Field of Classification Search
CPC .... A61M 5/365; A61M 5/007; A61M 5/3146; A61M 5/14546; A61M 2205/3379;
(Continued)

(56) References Cited

U.S. PATENT DOCUMENTS 383,858 A   6/1888   Campbell
508,584 A   11/1893  Stevens
(Continued)

FOREIGN PATENT DOCUMENTS

CA   2045070 A1   2/1992
CA   2077712 A1   12/1993
(Continued)

OTHER PUBLICATIONS

International Preliminary Report on Patentability and Written Opinion mailed on Sep. 24, 2015 from corresponding PCT Application No. PCT/US2014/026324.
(Continued)

*Primary Examiner* — Lauren P Farrar
(74) *Attorney, Agent, or Firm* — Joseph L. Kent; James R. Stevenson

(57) ABSTRACT

An injector system for delivering a medical fluid may include at least one syringe defining a reservoir operatively connected to a piston; and at least one processor programmed or configured to, based on an air check protocol for detecting air in the reservoir, determine a baseline value comprising baseline compressibility data for the at least one syringe of the injector system, deliver the first amount of the medical fluid from the reservoir; refill the reservoir with a second amount of the medical fluid; based on the air check
(Continued)

protocol, perform an air check pressurization sequence by gathering air check compressibility data for the at least one syringe of the injector system; and based on the air check protocol, compare the air check compressibility data with the baseline compressibility data to determine a volume of air present in the reservoir.

21 Claims, 13 Drawing Sheets

(51) Int. Cl.
 *A61M 5/145* (2006.01)
 *A61M 5/31* (2006.01)
(52) U.S. Cl.
 CPC . *A61M 5/14546* (2013.01); *A61M 2205/3379* (2013.01); *A61M 2205/3386* (2013.01); *A61M 2205/50* (2013.01); *A61M 2205/502* (2013.01)
(58) Field of Classification Search
 CPC ...... A61M 2205/3386; A61M 2205/50; A61M 2205/502
 See application file for complete search history.

(56) References Cited

U.S. PATENT DOCUMENTS

| | | |
|---|---|---|
| 945,143 A | 1/1910 | Jacques |
| 2,511,291 A | 6/1950 | Mueller |
| 2,583,206 A | 1/1952 | Borck et al. |
| 3,156,236 A | 11/1964 | Williamson |
| 3,159,312 A | 12/1964 | Van Sciver, II |
| 3,276,472 A | 10/1966 | Jinkens et al. |
| 3,349,713 A | 10/1967 | Fassbender |
| 3,520,295 A | 7/1970 | Paul |
| 3,523,523 A | 8/1970 | Heinrich et al. |
| 3,623,474 A | 11/1971 | Heilman et al. |
| 3,635,444 A | 1/1972 | Potter |
| 3,671,208 A | 6/1972 | Wayne |
| 3,701,345 A | 10/1972 | Heilman |
| 3,719,207 A | 3/1973 | Takeda |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,868,967 A | 3/1975 | Harding |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,204,775 A | 5/1980 | Speer |
| 4,207,871 A | 6/1980 | Jenkins |
| 4,208,136 A | 6/1980 | King et al. |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,329,067 A | 5/1982 | Goudy, Jr. |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,441,823 A | 4/1984 | Power et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers et al. |
| 4,552,130 A | 11/1985 | Kinoshita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,665 A | 9/1986 | Matsumoto et al. |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Wakoshi et al. |
| 4,838,856 A | 6/1989 | Mulreany et al. |
| 4,840,620 A | 6/1989 | Kobayashi et al. |
| 4,844,052 A | 7/1989 | Wakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 1,913,154 A | 4/1990 | Ermert et al. |
| 4,922,916 A | 5/1990 | Ermert et al. |
| 4,925,444 A | 5/1990 | Orkin et al. |

(56) References Cited

U.S. PATENT DOCUMENTS

| | | |
|---|---|---|
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,026,348 A | 6/1991 | Venegas |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,163,928 A | 11/1992 | Hobbs et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | MacVicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,651,776 A | 7/1997 | Appling et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |

(56) References Cited

U.S. PATENT DOCUMENTS

| | | |
|---|---|---|
| 5,724,976 A | 3/1998 | Mine et al. |
| 5,725,500 A | 3/1998 | Micheler |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,954,668 A | 9/1999 | Uber, III et al. |
| 5,964,703 A | 10/1999 | Goodman et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,159,183 A | 12/2000 | Neer et al. |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,375,624 B1 | 4/2002 | Uber, III et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,408,204 B1 | 6/2002 | Hirschman |
| 6,423,719 B1 | 7/2002 | Lawyer |
| 6,442,418 B1 | 8/2002 | Evans, III et al. |
| 6,459,931 B1 | 10/2002 | Hirschman |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,751,500 B2 | 6/2004 | Hirschman |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,047,058 B1 | 5/2006 | Dvorsky et al. |
| 7,094,216 B2 | 8/2006 | Trombley, III et al. |
| 7,122,012 B2 | 10/2006 | Bouton et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley, III et al. |
| 7,553,294 B2 | 6/2009 | Lazzaro et al. |
| 7,553,295 B2 | 6/2009 | Susi |
| 7,556,619 B2 | 7/2009 | Spohn et al. |
| 7,563,249 B2 | 7/2009 | Schriver et al. |
| 7,591,792 B2 | 9/2009 | Bouton |
| 7,666,169 B2 | 2/2010 | Cowan et al. |
| 7,688,057 B2 | 3/2010 | Foss et al. |
| 7,861,893 B2 | 1/2011 | Voegele et al. |
| 7,925,330 B2 | 4/2011 | Kalafut et al. |
| 7,937,134 B2 | 5/2011 | Uber et al. |
| 8,007,487 B2 | 8/2011 | Patrick et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,235,949 B2 | 8/2012 | Hack et al. |
| 8,295,914 B2 | 10/2012 | Kalafut et al. |
| 8,295,920 B2 | 10/2012 | Bouton et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,540,698 B2 | 9/2013 | Spohn et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,289,550 B1 | 3/2016 | Dvorsky et al. |
| 9,314,749 B2 | 4/2016 | Yagi et al. |
| 9,326,686 B2 | 5/2016 | Warren et al. |
| 9,333,293 B2 | 5/2016 | Williams, Jr. et al. |
| 9,474,857 B2 | 10/2016 | Riley et al. |
| 9,480,788 B2 | 11/2016 | Wagner |
| 9,480,791 B2 | 11/2016 | Reilly |
| 9,555,379 B2 | 1/2017 | Schriver et al. |
| 9,566,381 B2 | 2/2017 | Barron et al. |
| 9,855,387 B2 | 1/2018 | Small et al. |
| 9,861,752 B2 | 1/2018 | Buder et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,124,110 B2 | 11/2018 | Dedig et al. |
| 10,201,666 B2 | 2/2019 | Cowan et al. |
| D847,985 S | 5/2019 | Neff et al. |
| 10,391,234 B2 | 8/2019 | Sams et al. |
| 10,507,319 B2 | 12/2019 | Haury et al. |
| 10,549,084 B2 | 2/2020 | Sokolov et al. |
| 10,583,256 B2 | 3/2020 | Berry et al. |
| 10,933,190 B2 | 3/2021 | Berry et al. |
| 2001/0018937 A1 | 9/2001 | Nemoto |
| 2001/0027265 A1 | 10/2001 | Prince |
| 2001/0056233 A1 | 12/2001 | Uber et al. |
| 2002/0007116 A1 | 1/2002 | Zatezalo et al. |
| 2002/0010551 A1 | 1/2002 | Wang et al. |

(56) References Cited

U.S. PATENT DOCUMENTS

| | | |
|---|---|---|
| 2002/0026148 A1 | 2/2002 | Uber et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0064041 A1 | 4/2004 | Lazzaro et al. |
| 2004/0092905 A1 | 5/2004 | Azzolini |
| 2004/0097806 A1 | 5/2004 | Hunter et al. |
| 2004/0154788 A1 | 8/2004 | Symonds |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0171923 A1 | 9/2004 | Kalafut et al. |
| 2004/0215144 A1 | 10/2004 | Duchon et al. |
| 2004/0253183 A1 | 12/2004 | Uber, III et al. |
| 2004/0254533 A1 | 12/2004 | Schriver et al. |
| 2005/0107697 A1 | 5/2005 | Berke et al. |
| 2005/0113754 A1 | 5/2005 | Cowan |
| 2005/0113766 A1 | 5/2005 | Mottola et al. |
| 2005/0171487 A1 | 8/2005 | Haury et al. |
| 2005/0234407 A1 | 10/2005 | Spohn et al. |
| 2005/0234428 A1 | 10/2005 | Spohn et al. |
| 2006/0052794 A1 | 3/2006 | McGill et al. |
| 2006/0079765 A1 | 4/2006 | Neer et al. |
| 2006/0079843 A1 | 4/2006 | Brooks et al. |
| 2006/0135940 A1 | 6/2006 | Joshi |
| 2006/0167415 A1 | 7/2006 | Nemoto |
| 2006/0173360 A1 | 8/2006 | Kalafut et al. |
| 2006/0211970 A1 | 9/2006 | Sciulli |
| 2006/0276936 A1 | 12/2006 | Vanderveen |
| 2007/0068964 A1 | 3/2007 | Tanaami et al. |
| 2007/0129705 A1 | 6/2007 | Trombley et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0015406 A1 | 1/2008 | Dlugos et al. |
| 2008/0045925 A1 | 2/2008 | Stepovich et al. |
| 2008/0086087 A1 | 4/2008 | Spohn et al. |
| 2008/0147147 A1 | 6/2008 | Griffiths et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0113887 A1 | 5/2010 | Kalafut et al. |
| 2010/0114064 A1 | 5/2010 | Kalafut et al. |
| 2010/0130809 A1 | 5/2010 | Morello |
| 2010/0222768 A1 | 9/2010 | Spohn et al. |
| 2010/0249586 A1 | 9/2010 | Cocker et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0123229 A1 | 5/2012 | Butterfield et al. |
| 2012/0123257 A1* | 5/2012 | Stokes, Jr. ............ A61M 5/142 600/432 |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0030290 A1 | 1/2013 | Nemoto |
| 2013/0123619 A1 | 5/2013 | Griggs |
| 2013/0245439 A1 | 9/2013 | Small et al. |
| 2013/0245604 A1 | 9/2013 | Kouyoumjian et al. |
| 2013/0261993 A1 | 10/2013 | Ruchti et al. |
| 2013/0274599 A1 | 10/2013 | Bouton et al. |
| 2014/0027009 A1 | 1/2014 | Riley et al. |
| 2014/0142537 A1 | 5/2014 | Gibson et al. |
| 2014/0276550 A1 | 9/2014 | Uram et al. |
| 2016/0030662 A1 | 2/2016 | Uber, III et al. |
| 2016/0114109 A1 | 4/2016 | Lavi |
| 2016/0278725 A1 | 9/2016 | Van Nijnatten |
| 2016/0331896 A1 | 11/2016 | Nemoto et al. |
| 2016/0331951 A1 | 11/2016 | Sokolov et al. |
| 2017/0035974 A1 | 2/2017 | Berry et al. |
| 2017/0056603 A1* | 3/2017 | Cowan .................. A61M 5/365 |
| 2017/0136424 A1 | 5/2017 | Schriver et al. |
| 2017/0143898 A1 | 5/2017 | Grosse-Wentrup et al. |
| 2017/0196702 A1 | 7/2017 | Agarwal et al. |
| 2017/0232173 A1 | 8/2017 | Perry et al. |
| 2017/0258982 A1 | 9/2017 | Kemper |
| 2017/0290971 A1 | 10/2017 | Hedmann et al. |
| 2017/0312430 A1 | 11/2017 | Schleicher et al. |
| 2017/0343446 A1 | 11/2017 | Ciolkosz et al. |
| 2017/0361017 A1 | 12/2017 | Verma et al. |
| 2018/0015274 A1 | 1/2018 | Haury et al. |
| 2018/0133392 A1 | 5/2018 | Dembo et al. |
| 2018/0161496 A1 | 6/2018 | Berry et al. |
| 2018/0261496 A1 | 9/2018 | Liu et al. |
| 2019/0083699 A1 | 3/2019 | Spohn et al. |
| 2019/0134297 A1 | 5/2019 | Kamen et al. |
| 2020/0129702 A1 | 4/2020 | Pedersen |
| 2020/0149948 A1 | 5/2020 | Mcdermott et al. |
| 2021/0338922 A1 | 11/2021 | Uber, III et al. |
| 2022/0001092 A1 | 1/2022 | Benamou et al. |

FOREIGN PATENT DOCUMENTS

| | | |
|---|---|---|
| CA | 2234050 A1 | 4/1997 |
| CN | 1671428 A | 9/2005 |
| CN | 103347552 A | 10/2013 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 1800704 A1 | 6/2007 |
| EP | 1870121 A1 | 12/2007 |
| EP | 2692375 A1 | 2/2014 |
| EP | 2990073 A1 | 3/2016 |
| EP | 1838365 B1 | 2/2019 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |

(56) References Cited

FOREIGN PATENT DOCUMENTS

| | | |
|---|---|---|
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H101207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H10584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5485885 B2 | 5/2014 |
| JP | 5490840 B2 | 5/2014 |
| JP | 5511409 B2 | 6/2014 |
| JP | 5882595 B2 | 3/2016 |
| JP | 5897798 B2 | 3/2016 |
| JP | 6618673 B2 | 12/2019 |
| JP | 6644469 B2 | 2/2020 |
| JP | 6676377 B2 | 4/2020 |
| JP | 6792104 B2 | 11/2020 |
| JP | 6839853 B2 | 3/2021 |
| NO | 9325141 A1 | 12/1993 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |
| WO | 2004091688 A2 | 10/2004 |
| WO | 2005016165 A1 | 2/2005 |
| WO | 2005035995 A1 | 4/2005 |
| WO | 2006042093 A1 | 4/2006 |
| WO | 2006074415 A2 | 7/2006 |
| WO | 2007079016 A2 | 7/2007 |
| WO | 2007092618 A2 | 8/2007 |
| WO | 2007116840 A1 | 10/2007 |
| WO | 2007116862 A1 | 10/2007 |
| WO | 2007116891 A1 | 10/2007 |
| WO | 2007133942 A2 | 11/2007 |
| WO | 2008078604 A1 | 7/2008 |
| WO | 2008106108 A1 | 9/2008 |
| WO | 2008153831 A2 | 12/2008 |
| WO | 2009026420 A1 | 2/2009 |
| WO | 2009042577 A2 | 4/2009 |
| WO | 2009051995 A1 | 4/2009 |
| WO | 2010027636 A1 | 3/2010 |
| WO | WO-2010117841 A1 * 10/2010 ........ A61M 5/14244 |
| WO | 2011002744 A1 | 1/2011 |
| WO | 2011011346 A1 | 1/2011 |
| WO | 2011097487 A2 | 8/2011 |
| WO | 2011125303 A1 | 10/2011 |
| WO | 2012048277 A2 | 4/2012 |
| WO | 2012155035 A1 | 11/2012 |
| WO | 2013043868 A1 | 3/2013 |
| WO | 2014035672 A2 | 3/2014 |
| WO | 2014049656 A1 | 4/2014 |
| WO | 2014144651 A2 | 9/2014 |
| WO | 2014179326 A1 | 11/2014 |
| WO | 2014190264 A1 | 11/2014 |
| WO | 2015081109 A1 | 6/2015 |
| WO | 2015106107 A1 | 7/2015 |
| WO | 2015164783 A1 | 10/2015 |
| WO | 2016004329 A1 | 1/2016 |
| WO | 2016112163 A1 | 7/2016 |
| WO | 2016172467 A1 | 10/2016 |
| WO | 2016191485 A1 | 12/2016 |
| WO | 2017012781 A1 | 1/2017 |
| WO | 2017038575 A1 | 3/2017 |
| WO | 2017096072 A1 | 6/2017 |
| WO | 2017152036 A1 | 9/2017 |
| WO | 2018060505 A1 | 4/2018 |
| WO | 2018075379 A1 | 4/2018 |
| WO | 2018075386 A1 | 4/2018 |
| WO | 2018089882 A1 | 5/2018 |

OTHER PUBLICATIONS

International Search Report and Written Opinion mailed Jul. 18, 2014 from corresponding PCT Application No. PCT/US2014/026324, which was filed on Mar. 13, 2014.

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al. "Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T et al., "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium vol. achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Dardik, H. et al., "Remote Hydraulic Syringe Actuator," Arch. Surg., vol. 115, Issue 1, Jan. 1980.

Dawson, P. and Blomley, M., "The value of mathematical modelling in understanding contrast enhancement in CT with particular ref-

(56) References Cited

OTHER PUBLICATIONS erence to the detection of hypovascular liver metastases, " European Journal of Radiology, vol. 41, Issue 3, pp. 222-236 (Mar. 2002).

"Digital Injector for Angiography", Sias. (Sep. 7, 1993).

Disposable Low-Cost Catheter Tip Sensor Measures Blood Pressure during Surgery, Sensor (Jul. 1989).

EZ Chem Brochure, E-Z-EM, Inc. (Jul. 2007).

Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.

Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

Fleischmann, D., "Contrast Medium Injection Technique," In: U. Joseph Schoepf: "Multidetector—Row CT of The Thorax," pp. 47-59 (Jan. 22, 2004).

Fleischmann, D., "Present and Future Trends in Multiple Detector—Row CT Applications; CT Angiography", European Radiology, vol. 12, Issue 2, Supplement 2, Jul. 2002, pp. s11-s15.

Gardiner, G. A., et al., "Selective Coronary Angiography Using a Power Injector," AJR Am J Roentgenol., vol. 146, Issue 4, pp. 831-833 (Apr. 1986).

Garrett, J. S., et al., "Measurement of cardiac output by cine computed tomography," The American Journal of Cardiology, vol. 56, Issue 10, pp. 657-661, 1985.

Gembicki, F.W., "Vector Optimization for Control with Performance and Parameter Sensitivity Indices," PhD Thesis Case Western Reserve University, 1974.

Gentilini A., et al., "A new paradigm for the closed-loop intraoperative administration of analgesics in humans," IEEE Transactions on Biomedical Engineering, vol. 49, Issue 4, pp. 289-299 (Apr. 2002).

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).

Grant, S.C.D. et al., "Reduction of Radiation Exposure to the Cardiologist during Coronary Angiography by the Use of A Remotely Controlled Mechanical Pump for Injection of Contrast Medium," Catheterization and Cardiovascular Diagnosis, vol. 25, Issue 2, pp. 107-109 (Feb. 1992).

Tackstein, N. et al., "Glomerular Filtration Rate Measured by Using Triphasic Helical CT with a Two-Point Patlak Plot Technique," Radiology, vol. 230, Issue 1, pp. 221-226, Jan. 2004.

Hansen, P.C, Regularization tools: a MATLAB package for analysis and solution of discrete ill-posed problems, Numerical Algorithms, vol. 6, Issue 1, pp. 35, 1994.

Hansen, P.C., "The truncated SVD as a method for regularization," BIT Numerical Mathematics, vol. 27, Issue 4, pp. 534-555, 1987.

Harris P., H. D. "The Human Pulmonary Circulation," Edinburgh, Churchill Livingstone, (Appendix I), 1986.

Hayes, M., "Statistical Digital Signal Processing and Modeling", New York, New York, Wiley and Sons, 1996, pp. 154-177, (Prony's method).

Heiken; J.P. et al., "Dynamic Contrast-Enhanced CT of the Liver: Comparison of Contrast Medium Injection Rates and Jniphasic and Biphasic Injection Protocols", Radiology, May 1993, vol. 187, No. 2, pp. 327-331.

"Infus O.R. Multi-Drug Syringe Pump with Smart Labels," Bard MedSystems Division Inc., pp. 2693-2696 (2005).

"International Preliminary Report on Patentability from PCT Application No. PCT/US2019/028124", Oct. 29, 2020.

Ireland, M.A., et al., "Safety and Convenience of a Mechanical Injector Pump for Coronary Angiography," Catheterization and Cardiovascular Diagnosis, vol. 16, Issue 3, pp. 199-201 (1989).

Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).

Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.

Korosec, Frank, "Basic Principles of Phase-contrast, Time-of-flight, and Contrast-enhanced MR Angiography", 1999.

Krause, W, "Application of pharmacokinetics to computed tomography: injection rates and schemes: mono-, bi-, or multiphasic?," Investigative Radiology, vol. 31, Issue 2, pp. 91-100, Feb. 1996.

Krieger, R. A., "$CO_2$-Power-Assisted Hand-Held Syringe: Better Visualization during Diagnostic and Interventional Angiography," Cathet Cardiovasc Diagn., vol. 19, Issue 2, pp. 123-128 (Feb. 1990).

Jebel-Flarsheim Company, "Angiomat 6000 Digital Injection System-Operator's Manual", Document No. 600950, Rev. 1, Jan. 1990.

Mahnken, A. H., et al., "Determination of cardiac output with multislice spiral computed tomography: a validation study," Investigative Radiology, vol. 39, Issue 8, pp. 451-454, Aug. 2004.

Mahnken, A. H., et al., "Measurement of cardiac output from a test-bolus injection in multislice computed tomography," European Radiology, vol. 13, Issue 11, pp. 2498-2504, 2003.

Mark V/Mark V Plus Injector Operation Manual KMP 805P Rev. B. Medrad, Inc, 1990.

McClellan, J.H., "Parametric Signal Modeling," Chapter 1 in Advanced Topics in Signal Processing, Pentice-Hall, Englewood Cliffs, NJ (1988).

MCT and MCT Plus Injection Systems Operation Manual KMP 810P, Medrad, Inc, 1991.

Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.

Neatpisarnvanit, C. and Boston, J.R., "Estimation of plasma insulin from plasma glucose", IEEE Transactions on Biomedical Engineering, vol. 49, Issue 11, pp. 1253-1259, 2002.

Ostergaard, L., et al., "High resolution measurement of cerebral blood flow using intravascular tracer poluspassages. Part 1: Mathematical approach and statistical analysis," Magnetic Resonance in Medicine, vol. 36, Issue 5,pp. 715-725 (Nov. 1996).

Ostergaard, L., et al., "High resolution measurement of cerebral blood flow using intravascular tracer poluspassages. Part II: Experimental comparison and preliminary results," Magn Reson Med, vol. 36, Issue 5, pp. 726-736(Nov. 1996).

Parker, K.J., et al., "A Particulate Contrast Agent With Potential for Ultrasound Imaging of Liver," Ultrasound in Medicine & Biology, vol. 13, Issue 9, pp. 555-566 (Sep. 1987).

Rosen, B.R et al., "Perfusion Imaging with NMR Contrast Agents," Magentic Resonance in Medicine, vol. 14, No. 2, pp. 249-265, May 1, 1990.

Sablayrolles, J-L, "Cardiac CT: Experience from Daily Practice", Advance CT, A GE Healthcare Publication. Aug. 2004.

Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.

Swiss; Medical Care., "CT Expres Contrast Media Delivery System Operation Manual Rev 1", 2004.

"The Solution for Your IV Formulas", Valley Lab. Inc., E-39-15, 3399, 3400, 2646.

Ulrich; Medical., "Instructions for Use for ulrichINJECT CT motion— CT Contrast Media Injector", 2018.

Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.

Wada, D.R. and Ward, D.S., "Open loop control of multiple drug effects in anesthesia", IEEE Transactions on Biomedical Engineering, vol. 42, Issue 7, pp. 666-677, 1995.

(56) References Cited

OTHER PUBLICATIONS

Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
Angiography, Catheterization and Cardiovascular Diagnosis, vol. 19, pp. 123-128, 1990.
Awai Kazuo; et al, "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.
Brenner et al, Radiation Exposure From Medical Imaging: Time to Regulate?, JAMA, Jul. 14, 2010, vol. 304 No 2, 208-209.
Extravasation Sensor Support System LD Operation Manual, Nemoto Kyorindo Co Ltd, Sep. 13, 2012, Rev 4.
McCullough, et al., "Risk Prediction of Contrast-Induced Nephropathy", The American Journal of Cardiology, Sep. 18, 2006, vol. 98.
Sachiko T. Cochran et al., Trends in Adverse Events After IV Administration of Contrast Media, Am. J. of Roentgenology, Jun. 2001, 176, 1385-1388.
"The Solution for Our IV Formulas", IV 6500 Formulator Volumetric Pump, Valley Lab Inc., 39C 9410976 0000071 s, E-39-15, pp. 3399-3400, As early as 1980.

\* cited by examiner

SYSTEM AND METHOD FOR AIR DETECTION IN FLUID INJECTOR

CROSS REFERENCE TO RELATED APPLICATIONS

This application is a U.S. national phase application under 35 U.S.C. § 371 of PCT International Application No. PCT/US2019/028124, filed Apr. 18, 2019 and claims the benefit of U.S. Patent Provisional Application Nos. 62/659,988, filed on Apr. 19, 2018 and 62/723,711, filed on Aug. 28, 2018, the disclosures of which are incorporated by reference in their entireties herein.

BACKGROUND OF THE DISCLOSURE

Field of the Disclosure

The present disclosure relates generally to a system and method for detection and removal of air in a fluid injector and a fluid reservoir and, in particular, to a system and method for detection and removal of air in a fluid reservoir or a fluid injector to determine whether the fluid reservoir is filled with a medical fluid prior to a fluid injection procedure.

Description of Related Art

In many medical diagnostic and therapeutic procedures, a medical practitioner, such as a physician or radiologist, injects a patient with one or more medical fluids using a powered fluid injector. In recent years, a number of injector-actuated syringes and powered fluid injectors for pressurized injection of medical fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate to highlight certain internal organs or portions of the body during the imaging process, or to assure a complete injection of a bolus of contrast agent using a flushing agent.

Typically, powered injectors have pistons that connect to a syringe plunger within the fluid reservoir, such as a syringe. The syringe generally includes a rigid barrel with the syringe plunger being slidably disposed within the barrel. The pistons drive the plungers in a proximal and/or distal direction relative to a longitudinal axis of the barrel to draw fluid into the syringe barrel or deliver the fluid from the syringe barrel.

When drawing the medical fluid into the syringe, it is important that the syringe is fully filled with the medical fluid and air removed from the syringe to avoid inadvertent injection of air into the patient. In certain procedures, even small quantities of air may present a concern if injected into the vasculature during the injection procedure, for example in specific imaging procedures, such as angiography, even the injection of small amounts of air may lead to complications. Accordingly, it is desirable to develop improved systems and methods for detection of air in a fluid injector and the fluid reservoir.

SUMMARY OF THE DISCLOSURE

In view of the above-identified needs, provided is a system and method for detection and removal of air in a fluid injector and a closed fluid reservoir. Specifically, the present application is directed to a system and method for detection and removal of air in a fluid injector and a fluid reservoir and/or at least a portion of a fluid path or tubing set, such as a syringe, that may be fluidly isolated from a fluid pathway by a stopcock or other mechanism to determine whether the fluid reservoir filled with a medical fluid may also contain unacceptable amounts of air or gas prior to a fluid injection procedure.

In some examples of the present disclosure, an injector system for delivering a medical fluid may include at least one syringe defining a reservoir operatively connected to a piston element, the at least one syringe including a plunger, at least one portal in fluid communication with the reservoir, and optionally at least a portion of a fluid path or tubing set, wherein the reservoir is configured to contain the medical fluid; and at least one processor programmed or configured to: based on an air check protocol for detecting air in the reservoir, determine a baseline value comprising baseline compressibility data for the at least one syringe and associated components of the injector system, wherein the reservoir is substantially filled with a first amount of the medical fluid having a known volume of air; deliver the known volume of air and at least a portion of the first amount of the medical fluid from the reservoir; refill the reservoir with a second amount of the medical fluid where the second amount of medical fluid may have an unknown volume of air; based on the air check protocol, perform an air check pressurization sequence by gathering air check compressibility data for the second amount of medical fluid and the at least one syringe of the injector system; and based on the air check protocol, compare the air check compressibility data for the second amount of medical fluid with the baseline compressibility data to determine a volume of the unknown volume of air present in the reservoir.

In other examples of the present disclosure, the baseline value may be determined to account for a deflection of one or more components of the injector system, the compliance of the reservoir and optionally at least a portion of the fluid path or tubing set, and known volume of air. The processor may be further programmed or configured to, based on the air check protocol, purge any air in the first amount of the medical fluid from the reservoir before determining the baseline value. The processor may be further programmed or configured to, based on the air check protocol, incorporate at least one correction factor into an algorithm when comparing the air check compressibility data with the baseline compressibility data to account for variations in at least one of: deflection of one or more injector system components and/or compliance of the fluid reservoir, different volumes of the medical fluid compared to the volume of the first amount of the medical fluid for the baseline compressibility data, and different positions of the piston compared to a positon of the piston for the baseline compressibility data. The processor may be further programmed or configured to, based on the air check protocol, deliver a prime volume of the second amount of the medical fluid from the reservoir, wherein the prime volume of the second amount of the medical fluid has a volume greater than the volume of air present in the reservoir. The step where the processor is further programmed or configured to deliver the prime volume of the second amount of the medical fluid further may include optimizing the prime volume equal to a minimum volume of the second amount of the medical fluid necessary to remove the volume of air present in the reservoir and from any fluid path or tubing set between the fluid reservoir and the outlet. The processor may be further programmed or configured to, based on the air check protocol, determine whether the volume of air present in the reservoir exceeds a predetermined volume value. In the event the volume of air in the reservoir exceeds the predetermined volume value, the processor may be further programmed or configured to, based on the air check protocol, purge the volume of air from the reservoir before the second amount of the medical fluid is delivered from the reservoir and/or determine whether a fault condition exists. After the volume of air has been purged from the reservoir, the processor may be further programmed or configured to, based on the air check protocol, perform an additional air check pressurization sequence by gathering additional air check compressibility data from the reservoir, for example for a third or additional amounts of the medical fluid, and compare the additional air check compressibility data with the baseline compressibility data to determine whether any air remains in the reservoir. The predetermined volume value may range from 0.1 mL to 20 mL. Comparing the air check compressibility data with the baseline compressibility data to determine the volume of air present in the reservoir may include using an embedded algorithm to compare the air check compressibility data with the baseline compressibility data to determine the volume of air present in the reservoir. According to certain embodiments, the system may include a downstream detector, such as a downstream air detector, wherein the downstream detector may be programmed and configured to confirm that no air is present in the prime volume of the second amount of medical fluid as it is delivered from the reservoir. The at least one syringe may also include at least one valve associated with the at least one portal or a fluid path or tubing set, the at least one valve may be configured to move between a fill position, a delivery position, and a closed position in response to one or more instruction from the at least one processor. The at least one valve may be in the closed position for at least one of determining the baseline compressibility data and performing the air check pressurization sequence.

In other examples of the present disclosure, a method for detecting air in a reservoir may include determining a baseline value comprising baseline compressibility data for a fluid injector system comprising at least one fluid reservoir having at least one fluid portal and optionally a fluid path or tubing set, wherein the at least one reservoir is substantially filled with a first amount of a medical fluid having a known amount of air; delivering the first amount of the medical fluid from the at least one reservoir; refilling the at least one reservoir with a second amount of the medical fluid; performing an air check pressurization sequence comprising pressurizing the second amount of medical fluid in the at least one reservoir and gathering air check compressibility data; and comparing the air check compressibility data with the baseline compressibility data to determine a volume of air present in the at least one reservoir.

In other examples of the present disclosure, determining the baseline value may include accounting for a deflection of one or more components of the fluid injection system, compliance of the at least one reservoir and a fluid path or tubing set, and known volume of air. The method may include purging the known volume of air from the at least one reservoir prior to determining the baseline value. The method may include incorporating at least one compensation factor into an algorithm, when comparing the air check compressibility data with the baseline compressibility data to account for variations in at least one of deflection of one or more fluid injector system components and/or compliance of the fluid reservoir, different volumes of the medical fluid compared to the volume of the first amount of the medical fluid for the baseline compressibility data, and different positions of a piston in the fluid injector system compared to a position of the piston for the baseline compressibility data. The method may include delivering a prime volume of the second amount of the medical fluid from the at least one reservoir, wherein the prime volume of the second amount of the medical fluid has a volume greater than the volume of the air present in the at least one reservoir. Delivering the prime volume of the second amount of the medical fluid may include optimizing the prime volume to equal to a minimum volume of the second amount of the medical fluid necessary to remove the volume of the air present in the at least one reservoir and from any fluid path or tubing set between the fluid reservoir and the outlet. The method may include determining whether a fault condition exists when the volume of air present in the at least one reservoir exceeds a specified volume. The method may include closing a fluid path associated with the at least one fluid portal of the at least one reservoir prior to at least one of determining the baseline value and performing the air check pressurization sequence. The second amount of the medical fluid may be different than the first amount of the medical fluid.

Various other aspects of the present disclsoure are recited in one or more of the following clauses:

Clause 1: An injector system for delivering a medical fluid, comprising: at least one syringe defining a reservoir operatively connected to a piston, the at least one syringe comprising a plunger and at least one portal in fluid communication with the reservoir, the reservoir configured to contain the medical fluid; and at least one processor programmed or configured to: based on an air check protocol for detecting air in the reservoir, determine a baseline value comprising baseline compressibility data for the at least one syringe of the injector system, wherein the reservoir is substantially filled with a first amount of the medical fluid having a known volume of air; deliver the first amount of the medical fluid from the reservoir; refill the reservoir with a second amount of the medical fluid; based on the air check protocol, perform an air check pressurization sequence by gathering air check compressibility data for the at least one syringe of the injector system; and based on the air check protocol, compare the air check compressibility data with the baseline compressibility data to determine a volume of air present in the reservoir.

Clause 2: The injector system of Clause 1, wherein the baseline value is determined to account for a deflection of one or more components of the injector system and compliance of the reservoir and fluid path, and known volume of air.

Clause 3: The injector system of Clause 1 or 2, wherein the processor is further programmed or configured to, based on the air check protocol, purge any air in the first amount of the medical fluid from the reservoir before determining the baseline value.

Clause 4: The injector system of any of Clauses 1 to 3, wherein the processor is further programmed or configured to, based on the air check protocol, incorporate a correction factor when comparing the air check compressibility data with the baseline compressibility data to account for variations in at least one of deflection of one or more injector system components, different volumes of the medical fluid compared to the volume of the first amount of the medical fluid for the baseline compressibility data, and different positions of a piston compared to a positon of the piston for the baseline compressibility data.

Clause 5: The injector system of any of Clauses 1 to 4, wherein the processor is further programmed or configured to, based on the air check protocol, deliver a prime volume of the second amount of the medical fluid from the reservoir, wherein the prime volume of the second amount of the medical fluid has a volume greater than the volume of air present in the reservoir.

Clause 6: The injector system of Clause 5, wherein the step where the processor is further programmed or configured to deliver the prime volume of the second amount of the medical fluid further comprises optimizing the prime volume equal to a minimum volume of the second amount of the medical fluid necessary to remove the volume of air present in the reservoir.

Clause 7: The injector system of any of Clauses 1 to 6, wherein the processor is further programmed or configured to, based on the air check protocol, determine whether the volume of air present in the reservoir exceeds a predetermined volume value.

Clause 8: The injector system of Clause 7, wherein, in the event the volume of air in the reservoir exceeds the predetermined volume value, the processor is further programmed or configured to, based on the air check protocol, purge the volume of air from the reservoir before the second amount of the medical fluid is delivered from the reservoir or determine whether a fault condition exists.

Clause 9: The injector system of Clause 8, wherein, after the volume of air has been purged from the reservoir, the processor is further programmed or configured to, based on the air check protocol, perform an additional air check pressurization sequence by gathering additional air check compressibility data from the reservoir, and compare the additional air check compressibility data with the baseline compressibility data to determine whether any air remains in the reservoir.

Clause 10: The injector system of Clause 7, wherein the predetermined value ranges from 0.1 milliliters to 20 milliliters.

Clause 11: The injector system of any of Clauses 1 to 10, wherein comparing the air check compressibility data with the baseline compressibility data to determine the volume of air present in the reservoir comprises using an embedded algorithm to compare the air check compressibility data with the baseline compressibility data to determine the volume of air present in the reservoir.

Clause 12: The injector system of any of Clauses 5 to 11, further comprising a downstream air detector, wherein the downstream air detector is programmed and configured to confirm that no air is present in the prime volume of the second amount of medical fluid as it is delivered from the reservoir.

Clause 13: The injector system of any of Clauses 1 to 12, wherein the at least one syringe further includes at least one valve associated with the at least one portal, the at least one valve is configured to move between a fill position, a delivery position, and a closed position in response to one or more instruction from the at least one processor.

Clause 14: The injector system of Clause 13, wherein the at least one valve is in the closed position for at least one of determining the baseline compressibility data and performing the air check pressurization sequence.

Clause 15: A method for detecting air in a reservoir, the method comprising: determining a baseline value comprising baseline compressibility data for a fluid injector system comprising at least one reservoir having at least one fluid portal, wherein the at least one reservoir is substantially filled with a first amount of a medical fluid having a known amount of air; delivering the first amount of the medical fluid from the at least one reservoir; refilling the at least one reservoir with a second amount of the medical fluid; performing an air check pressurization sequence comprising pressurizing the medical fluid in the at least one reservoir and gathering air check compressibility data; and comparing the air check compressibility data with the baseline compressibility data to determine a volume of air present in the at least one reservoir.

Clause 16: The method of Clause 15, wherein determining the baseline value comprises accounting for a deflection of the fluid injection system, compliance of the at least one reservoir and a fluid path, and known volume of air.

Clause 17: The method of Clause 15 or 16, further comprising purging the known volume of air from the at least one reservoir prior to determining the baseline value.

Clause 18: The method of any of Clauses 15 to 17, further comprising incorporating a compensation factor when comparing the air check compressibility data with the baseline compressibility data to account for variations in at least one of deflection of one or more fluid injector system components, different volumes of the medical fluid compared to the volume of the first amount of the medical fluid for the baseline compressibility data, and different positions of a piston in the fluid injector system compared to a position of the piston for the baseline compressibility data.

Clause 19: The method of any of Clauses 15 to 18, further comprising delivering a prime volume of the second amount of the medical fluid from the at least one reservoir, wherein the prime volume of the second amount of the medical fluid has a volume greater than the volume of the air present in the at least one reservoir.

Clause 20: The method of Clause 19, wherein delivering the prime volume of the second amount of the medical fluid further comprises optimizing the prime volume to equal to a minimum volume of the second amount of the medical fluid necessary to remove the volume of the air present in the at least one reservoir.

Clause 21: The method of any of Clauses 15 to 20, further comprising determining whether a fault condition exists when the volume of air present in the at least one reservoir exceeds a specified volume.

Clause 22: The method of any of Clauses 15 to 21, further comprising closing a fluid path associated with the at least one fluid portal of the at least one reservoir prior to at least one of determining the baseline value and performing the air check pressurization sequence.

Clause 23: The method of any of Clauses 15 to 22, wherein the second amount of the medical fluid is different than the first amount of the medical fluid.

Further details and advantages of the various examples described in detail herein will become clear upon reviewing the following detailed description of the various examples in conjunction with the accompanying drawing figures.

BRIEF DESCRIPTION OF THE DRAWINGS

In FIGS. 1-9, like characters refer to the same components and elements, as the case may be, unless otherwise stated.

DETAILED DESCRIPTION

Figure 1:
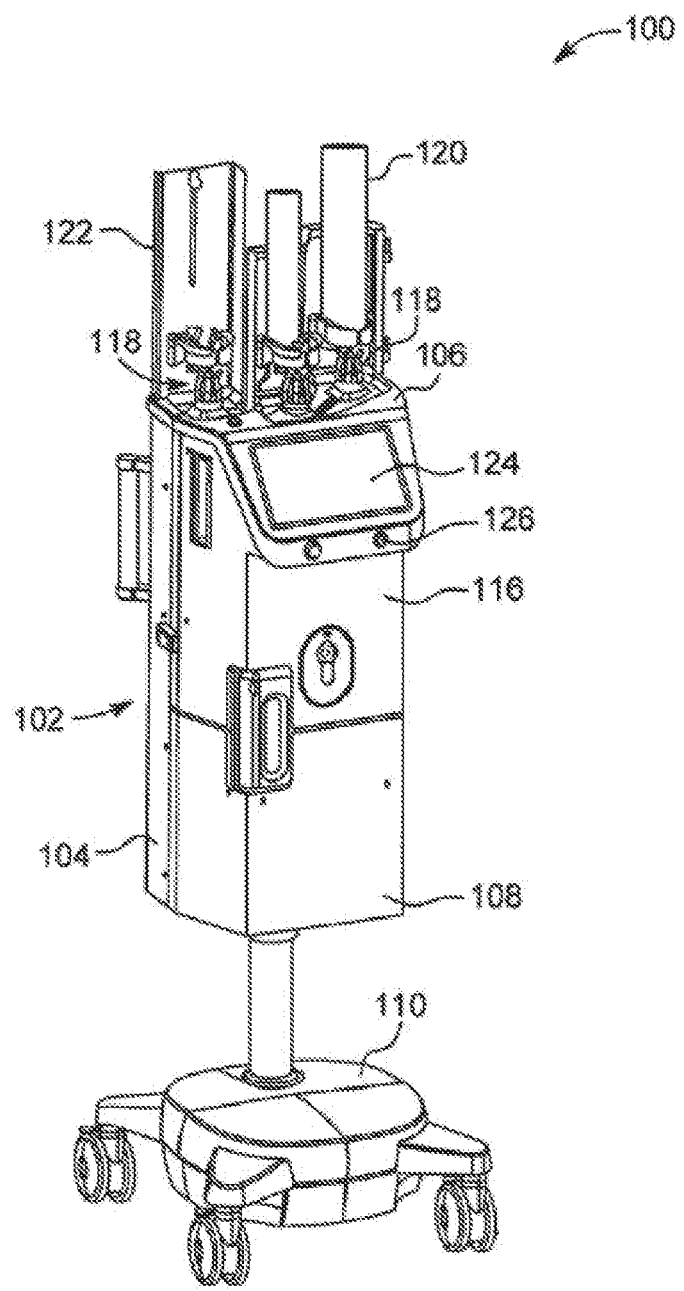
FIG. 1 is a perspective view of a fluid injector configured for use multi-fluid delivery system, according to one aspect of the present disclosure.

As used herein, the singular form of "a", "an", and "the" include plural referents unless the context clearly dictates otherwise. Spatial or directional terms, such as "left", "right", "inner", "outer", "above", "below", and the like, relate to the features of the disclosure as shown in the drawing figures and are not to be considered as limiting as the various features can assume various alternative orientations. All numbers used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements. The term "at least" is synonymous with "greater than or equal to". The term "not greater than" is synonymous with "less than or equal to". All documents referred to herein are "incorporated by reference" in their entirety.

As used herein, "at least one of" is synonymous with "one or more of". For example, the phrase "at least one of A, B, and C" means any one of A, B, or C, or any combination of any two or more of A, B, or C. For example, "at least one of A, B, and C" includes A alone; or B alone; or C alone; or A and B; or A and C; or B and C; or all of A, B, and C. The term "includes" is synonymous with "comprises".

When used in relation to a syringe, for example, of a multi-use disposable set (MUDS), the term "proximal" refers to a portion of a syringe nearest a piston element for delivering fluid from a syringe. When used in relation to a fluid path, the term "proximal" refers to a portion of the fluid path nearest to an injector system when the fluid path is connecting with the injector system. When used in relation to a syringe, the term "distal" refers to a portion of a syringe nearest to a delivery nozzle. When used in relation to a fluid path, the term "distal" refers to a portion of the fluid path nearest to a user when the fluid path is connected with an injector system. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial" refers to a direction along a longitudinal axis of the syringe extending between the proximal and distal ends.

As used herein, the terms "reservoir" or "fluid reservoir" include a syringe, container, or at least a portion of a fluid path, such as a tubing set. Any type of reservoir that can have a force applied or displacement applied may be utilized in the air detection methods described herein. The term "open" when used to refer to a fluid delivery component means that the system is in fluid connection with an outlet, for example through a nozzle or the open end of a fluid path, a tubing component or catheter. In an open system, fluid flow may be constrained, for example by forcing a fluid through a small diameter fluid path where flow may be determined by physical parameters of the system and the fluid, such as tubing diameter, fluid path constrictions, applied pressure, viscosity, etc. The term "closed" when used to refer to a fluid delivery component means that the system is not in fluid connection with or fluidly isolated from an outlet, for example where fluid flow is stopped by a valve, such as a stopcock, high crack pressure valve, pinch valve, one-way valve, or the like. As used herein, the term "slack" means mechanical slack, including a clearance or lost motion in a mechanism caused by gaps between parts, compression and/or deflection of one or more mechanical components under an applied load (such as by applied pressure) that results in a delay of pressurized delivery of a fluid from a fluid injection after application of force. The reservoir in this scenario is dependent on where the system is closed. As used herein, the terms "compliance" or "capacitance" mean the increase in volume of a fluid reservoir, fluid path, or tubing set, in either a closed system or an open system, when the fluid contained therein is placed under pressure causing the interior volume to swell.

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

The present disclosure describes systems and methods to detect both small amounts of air, for example ranging from 0.1 mL to 1.0 mL, and also large amounts of air, up to and including if the syringe is completely filled with air, such as if there is an issue during a filling process of the syringe, thereby reducing the possibility that air may be inadvertently injected into a patient during a medical procedure, such as injection of a contrast agent and/or saline prior to a contrast enhanced imaging procedure. The methods of the present disclosure may be performed after initiation by a user or performed automatically by a processor of a fluid injector as the injector is prepared for one or more fluid injection protocols.

Referring to the drawings in which like reference characters refer to like parts throughout the several views thereof, the present disclosure is generally directed to a medical injector/injection system 100 (hereinafter "fluid injector system 100") for example an injector system including one or more syringes, including front-loading syringe and rolling diaphragm-type syringes. The present disclosure is illustrated according to an embodiment to a fluid injector system 100 in the form of a multi-fluid injector system, for example, having a MUDS 130 (shown in FIG. 2) configured for delivering fluid to a patient using a fluid path, such as a tubing set and/or manifold. However, the various methods and protocols of the present disclosure may be utilized or incorporated into other syringe-based injector systems.

The fluid injector system 100 includes multiple components as individually described herein. Generally, the fluid injector system 100 has a powered injector administrator or device and a fluid delivery set intended to be associated with the injector to deliver one or more fluids from one or more fluid reservoirs under pressure into a patient, as described herein. The various devices, components, and features of the fluid injector system 100 and the fluid delivery set associated therewith are likewise described in detail herein according to one embodiment. In one example, the MUDS 130 is disclosed in WO 2016/112163, and an example of the SUDS is described in WO 2015/106107, both of which are incorporated in their entireties by reference herein. The air detection method described below in detail may begin at the initial installation of the MUDS 130 and/or may be repeated after each filling of one or more of the fluid reservoirs in the MUDS 130 during a series of injection procedures or over the use life-time of the MUDS 130.

In other examples, the methods of the present disclosure may be suited for use in single or dual syringe-type front-loading fluid injector systems, such as are disclosed in U.S. Pat. Nos. 5,383,858, 7,553,294, 7,563,249, 7,666,169, 8,945,051, 9,173,995, 9,199,033, 9,474,857, and 10,124,110, U.S. patent application Ser. Nos. 15/305,285, 15/541,573, and 15/568,505, and in PCT Application Publication Nos. WO 2016/191485 and WO 2016/112163, the disclosures of which are incorporated herein by reference in their entireties, and in single or dual rolling diaphragm syringe-type front-loading fluid injector systems, examples of which are disclosed in International Application No. PCT/US2017/056747, WO 2016/172467, and WO 2015/164783, the disclosures of which are incorporated herein by reference in their entireties.

With reference to FIG. 1, the fluid injector system 100 includes an injector housing 102 having opposed lateral sides 104, a distal or upper end 106, and a proximal or lower end 108. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements associated with the fluid injector system 100 described herein. Such piston elements may be reciprocally operable via electro-mechanical drive components such as a ball screw shaft driven by a motor, a voice coil actuator, a rack-and-pinion gear drive, a linear motor, and the like. In some aspects, at least some of the mechanical drive components, electrical and power components, and control components may be provided on the base 110.

The fluid injector system 100 further includes at least one bulk fluid connector 118 for connection with at least one bulk fluid source 120. In some aspects, a plurality of bulk fluid connectors 118 may be provided. The at least one bulk fluid source 120 may be configured for receiving a medical fluid, such as saline, contrast solution, or other medical fluid, for delivery to the fluid injector system 100. The housing 102 may have at least one support member 122 for supporting the at least one bulk fluid source 120 once it is connected to the fluid injector system 100.

With reference to FIG. 1, the fluid injector system 100 includes one or more user interfaces 124, such as a graphical user interface (GUI) display window. The user interface 124 may display information pertinent to a fluid injection procedure involving the fluid injector system 100, such as current flow rate, fluid pressure, and volume remaining in the at least one bulk fluid source 120 connected to the fluid injector system 100 and may present information on air present in the one or more reservoirs as determined by the various methods and protocols described herein. In certain embodiments, the one or more user interfaces 124 may be a touch screen GUI that allows an operator to input commands and/or data for operation of the fluid injector system 100. While the user interface 124 is shown on the injector housing 102, interface 124 may also be in the form of or include an additional remote display that is wired or wirelessly linked to the housing 102 and control and mechanical elements of the fluid injector system 100. In some aspects, the user interface 124 may be a tablet computer that is detachably connected to the housing 102 and is in wired or wirelessly linked communication with the housing 102. The fluid injector system 100 may further include one or more processors in electronic communication with and configured to control one or more functions of the fluid injector system 100, such as for example, any of the air detection method steps described herein. Additionally, the fluid injector system 100 and/or user interface 124 may include at least one control button 126 for tactile operation by an attendant operator of the fluid injector system 100. In certain aspects, the at least one control button 126 may be part of a keyboard for inputting commands and/or data by the operator. The at least one control button 126 may be hard-wired or wirelessly connected to the electronic control device(s) associated with the fluid injector system 100 to provide direct input to the electronic control device(s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) acknowledging that a multi-patient disposable set has been loaded or unloaded; (2) initiating or providing information regarding the air detection methods according to various embodiments herein; (3) filling/purging of the fluid injector system 100; (4) inputting information and/or data related to the patient and/or injection procedure, and (5) initiating/stopping an injection procedure. The user interface 124 and/or any electronic processing units associated with the fluid injector system 100 may be wired or wirelessly connected to an operation and/or data storage system such as a hospital network system.

Figure 2:
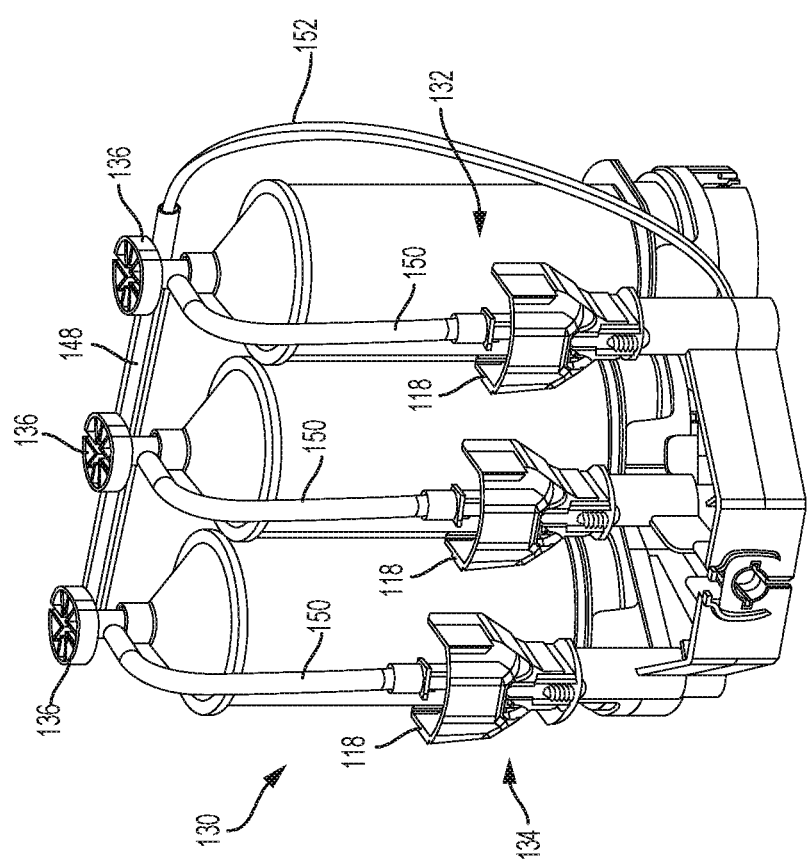
FIG. 2 is a perspective view of a multi-fluid delivery system for use with the fluid injector of FIG. 1.
Figure 4A:
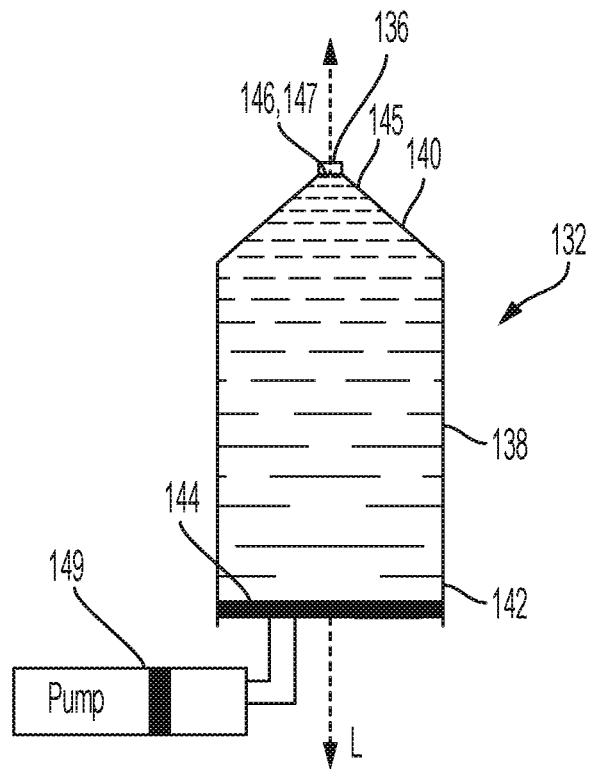
FIG. 4A is a schematic view of a syringe according to the present disclosure with a purge port in an open position.
Figure 4B:
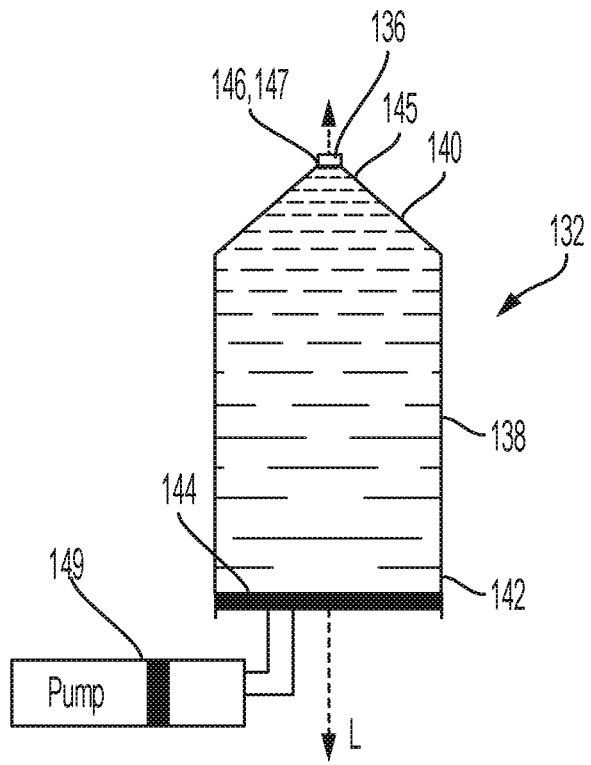
FIG. 4B is a schematic view of the syringe of FIG. 4A with the purge port closed.

With reference to FIG. 2, the MUDS 130 may include a frame 154 for supporting the one or more syringes 132. The syringes 132 may be removably or non-removably connected to the frame 154. With reference to FIGS. 4A-4B, each syringe 132 may have an elongated, substantially cylindrical syringe body 138 having a front or distal end 140 and a rear or proximal end 142. A syringe plunger 144 is disposed within the syringe body 138 and is reciprocally movable within the syringe body 138 in response to movement of a piston element associated with the fluid injector system 100. The distal end 140 of the syringe body 138 may be generally conical-shaped and tapered to an apex or cone point 145. The syringe apex or cone point 145 is located along a central longitudinal axis L of the syringe body 138.

With continued reference to FIGS. 4A,B,D,F, each syringe 132 may have a filling port 147 in fluid communication with the fluid path 136 for filling a syringe interior 139 with fluid from a bulk fluid source 120 (shown in FIG. 2). Each syringe 132 may further have a discharge outlet 146 at the terminal end of the apex or cone point 145. The discharge outlet 146 of each syringe 132 is in fluid communication with a manifold 148 (shown in FIG. 2). In some aspects, the manifold 148 may fluidly connect a plurality of syringes 132. Fluid communication between the syringe interior 139 and the fluid path 136 and manifold 148 may be controlled by a valve 136 at the distal end 145 of the syringe 132. A pump 149, such as a piston element for reciprocally moving a plunger 144, may be releasably attached to the plunger 144 of the syringe 132 to selectively draw in a medical fluid through the filling port 147 or expel a medical fluid and/or a gas through the discharge outlet 146 of the syringe 132. In certain aspects, the manifold 148 may also provide support for the syringes 132 such that the syringes 132 can be handled as a single, unitary structure. In some aspects, the manifold 148 supports the distal end 140 of each syringe 132 while the frame 154 supports the proximal end 142 of each syringe 132. In some aspects, at least a portion of the manifold 148 may be monolithically formed with at least one syringe 132, for example by an appropriate adhesive or welding. The syringes 132 may be arranged in a side-by-side orientation, or any other orientation that retains the relative positioning of the syringes 132.

Figure 3:
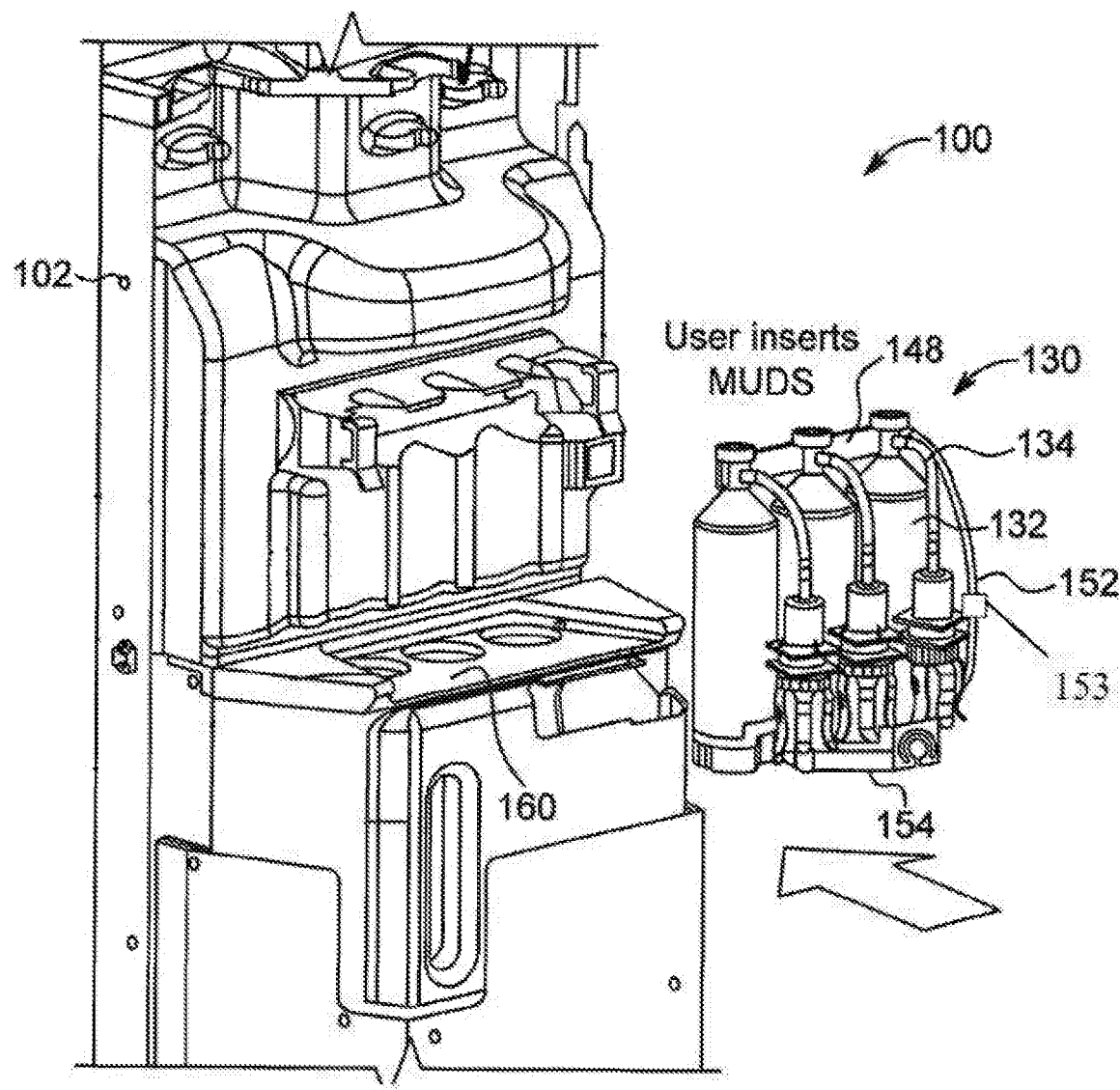
FIG. 3 is a perspective view of a multi-fluid delivery system as it is being inserted into a receiving slot on the fluid injector of FIG. 1.

With reference to FIG. 3, the MUDS 130 is illustrated in accordance with another aspect. The MUDS 130 may include a plurality of syringes 132 in a side-by-side, or other arrangement, with each syringe 132 being fluidly connectable to one of the bulk fluid sources 120 (shown in FIG. 2). Each syringe 132 may be in fluid communication with the manifold 148. The manifold 148 may monolithically connect the syringes 132. The manifold 148 may have a fluid pathway that is in fluid communication with each syringe 132. The fluid pathway may be in fluid communication with one or more fluid outlet lines 152 (shown in FIG. 2). A valve 136 may be provided on each fluid fill line 150 that extends from the bulk fluid source 120 to the filling port 147 of the syringes 132 to fill the syringes 132 with fluid from the bulk fluid sources 120. According to various embodiments, at least a portion of the valve 136 may be rotatable, for example, about the longitudinal axis L of each respective syringe 132. The valve 136 may be operable between a fill position for filling the syringe 132 with fluid, a delivery position for delivering the fluid from the syringe 132, and a closed position to prevent fluid from entering or exiting the syringe 132. In some aspects, the valve 136 may be rotatable between a first position, where the filling port 147 is in fluid communication with the syringe 132 while the discharge outlet 146 is in fluid isolation from the syringe 132, and a second position, where the discharge outlet 146 is in fluid communication with the syringe 132 while the filling port 147 is in fluid isolation from the syringe interior. The valve 136 may have a third position where the interior of the syringe 132 is isolated from both the filling port 147 and the discharge outlet 146. In the first position, the valve 136 may be configured for filling the syringe 132 with fluid from a bulk fluid source 120 through the fluid path 134 while preventing fluid from being delivered to the manifold 148. In the second position, the valve 136 may be configured for delivering fluid from the syringe 132 to the manifold 148 through the discharge outlet 146 while preventing fluid from being delivered through the filling port 147. The valve 136 may be configured for fluidly isolating the interior of the fluid reservoir, e.g., preventing fluid flow through the filling port 147 and the discharge outlet 146 such that fluid cannot be delivered into or from the syringe132. In some aspects, the valve 136 may be rotatable to partially open or partially close the discharge outlet 146 and/or the filling port 147. In various aspects, the valves 136 on each syringe 132 may be controlled independently of each other, for example, such that various medical fluids can be delivered into one or more syringes 132 and/or, simultaneously or sequentially, be delivered out of one or more other syringes 132. The valves 136 of the plurality of syringes 132 may be controlled, for example, through the electronic control device(s) or processor associated with the fluid injector system 100. The valves 136 may be stopcocks, high crack pressure valves, pinch valves, one-way valves, or any similar type of valve.

With further reference to FIG. 2, the MUDS 130 is removably connectable to the housing 102 of the fluid injector system 100. As will be appreciated by one having ordinary skill in the art, it may be desirable to construct at least a portion of the MUDS 130 from a clear medical grade plastic in order to facilitate visual verification that a fluid connection has been established with the fluid injector system 100. Visual verification is also desirable for confirming that no air bubbles are present within various fluid connections, for example, to confirm that no air remains in the syringe or fluid path after the air detection and priming sequence. Alternatively, at least a portion of the MUDS 130 and/or door 116 may include windows (not shown) for visualization of the connection between various components.

With reference to FIG. 2, in some aspects, the fluid outlet line 152 may also be connected to a waste reservoir 156 on the fluid injector system 100. The waste reservoir 156 is desirably separate from the syringes 132 to prevent contamination. In some aspects, the waste reservoir 156 is configured to receive waste fluid and any air expelled from the syringes 132 during, for example, a priming or purging operation, such as after the fluid detection protocols described herein.

As used herein, the electronic control device includes a processor to, or is operable to, execute appropriate custom-designed or conventional software to perform and implement the processing steps of the embodiments of the methods and systems of the present disclosure, thereby forming a specialized and particular computing system. Accordingly, the presently-disclosed methods and systems may include one or more electronic control devices or similar computing devices having a computer-readable storage medium capable of storing computer-readable program code or instructions that cause the processing unit to execute, configure, or otherwise implement the methods, processes, and transformational data manipulations discussed hereinafter in connection with the present disclosure. Still further, the electronic control device may be in the form of a computer, a personal digital assistant, a portable computer, a laptop, a palmtop, a mobile device, a mobile telephone, a server, or any other type of computing device having the necessary processing hardware to appropriately process data to effectively implement the presently-disclosed computer-implemented method and system. In one example, the electronic control devices may be housed in the user interface 124 and corresponding processor.

It will be apparent to one skilled in the relevant arts that the system may utilize databases physically located on one or more computers or accessible by the computer, for example, over the internet or cloud computing technologies, which may or may not be the same as their respective servers. For example, programming software on electronic control devices can control a database physically stored on a separate processor of the network or otherwise, or stored at a local or single site accessible by multiple fluid injection systems. Such a local or single site may allow for ready updating of the information and data stored thereof and accessible by processors associated by a plurality of distant fluid injectors.

In some aspects, the electronic control device may be programmed so that automatic refill occurs based upon a preprogrammed trigger minimum volume in the respective syringes 132. For example, when the volume of fluid remaining in at least one of the syringes 132 is less than a programmed volume, a syringe refill procedure may be automatically initiated by the electronic control device. The electronic control device associated with the fluid injector system 100 may determine that the preprogrammed trigger minimum volume has been reached by tracking the fluid volume dispensed from the respective syringes 132 during operation of the fluid injector system 100. Alternatively, fluid level sensors may be incorporated into the fluid injector system 100 and inputs from these fluid level sensors may be provided to the electronic control device so that the electronic control device may determine when the preprogrammed trigger minimum volume has been reached in at least one of the syringes 132. The fill volume and rate of refill can be preprogrammed in the electronic control device. The automatic refill procedure can be stopped either automatically by the electronic control device or may be manually interrupted. In addition, an automatic refill procedure may be initiated when, at the completion of a fluid injection procedure, there is not enough fluid in at least one of the syringes 132 to perform the next programmed fluid injection procedure. During a refill procedure it is possible that one or more of the bulk fluid sources 120 associated with the respective syringes 132 may become empty, (e.g., initially lack sufficient fluid to complete a full refill of the one or more syringes 132). The fluid injector system 100 may have an indicator, such as an audible and/or visual indicator, to indicate to the operator that a change of the bulk fluid source 120 is necessary before the fluid injector system 100 may be used. According to various embodiments, the air detection methods and protocols described herein may be performed for each fluid reservoir or syringe, every time the fluid reservoir or syringe is refilled with the medical fluid to determine if air has been introduced into the fluid reservoir along with the refilled fluid.

Figure 4C:
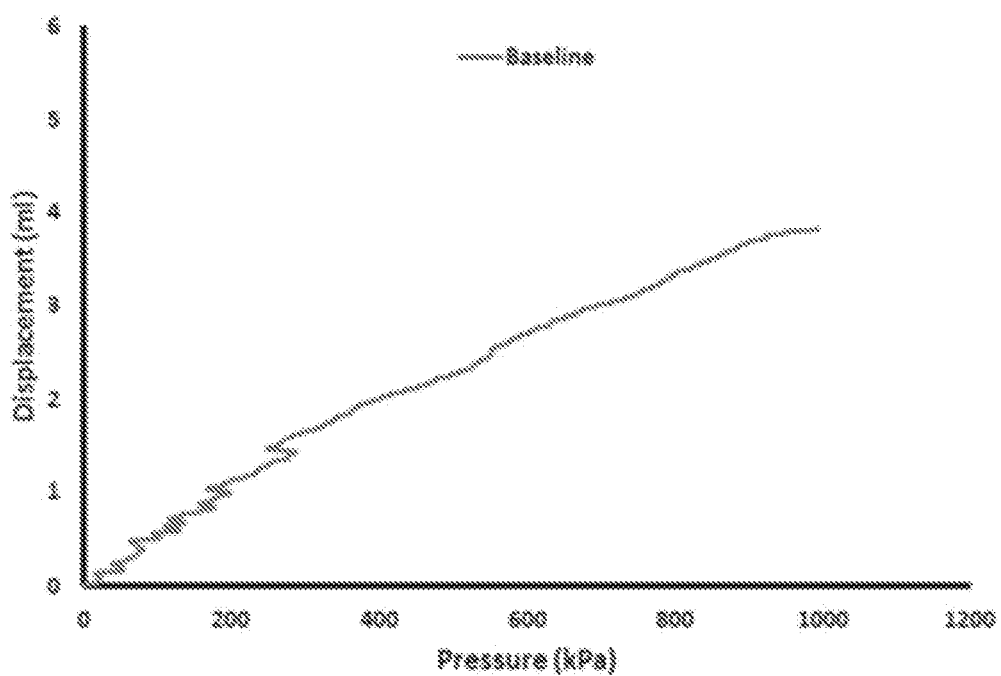
FIG. 4C is a graphical illustration of baseline compressibility data obtained during the air check protocol of the present disclosure.
Figure 4D:
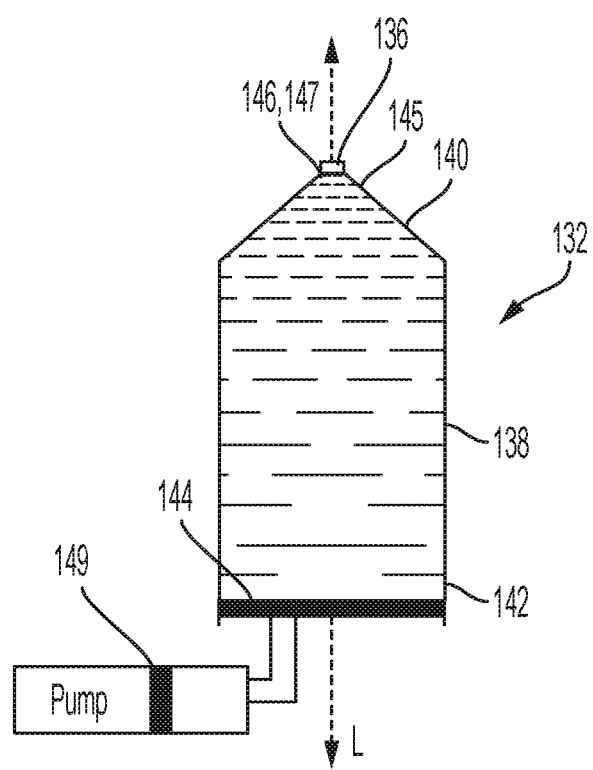
FIG. 4D is a schematic view of the syringe of FIG. 4A with the injection port in an open position.
Figure 4E:
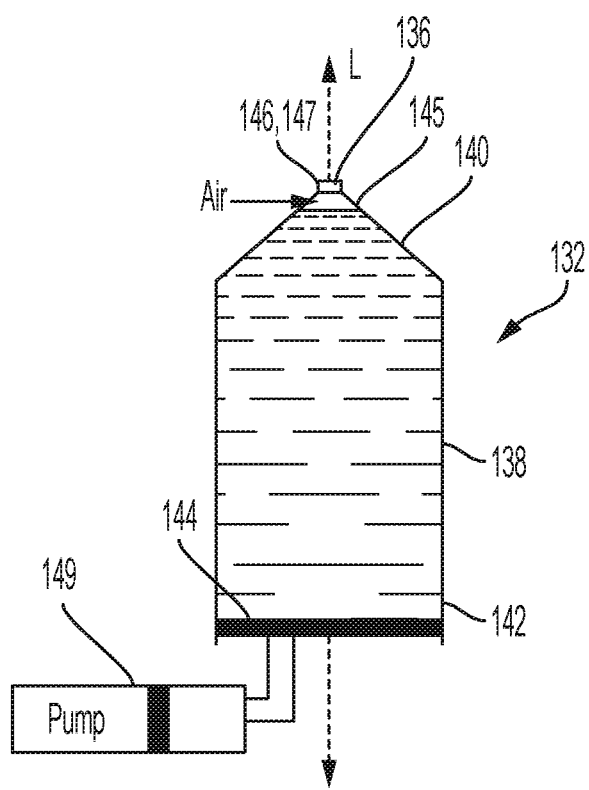
FIG. 4E is a schematic view of the syringe of FIG. 4A with the injection port in a closed position.
Figure 4F:
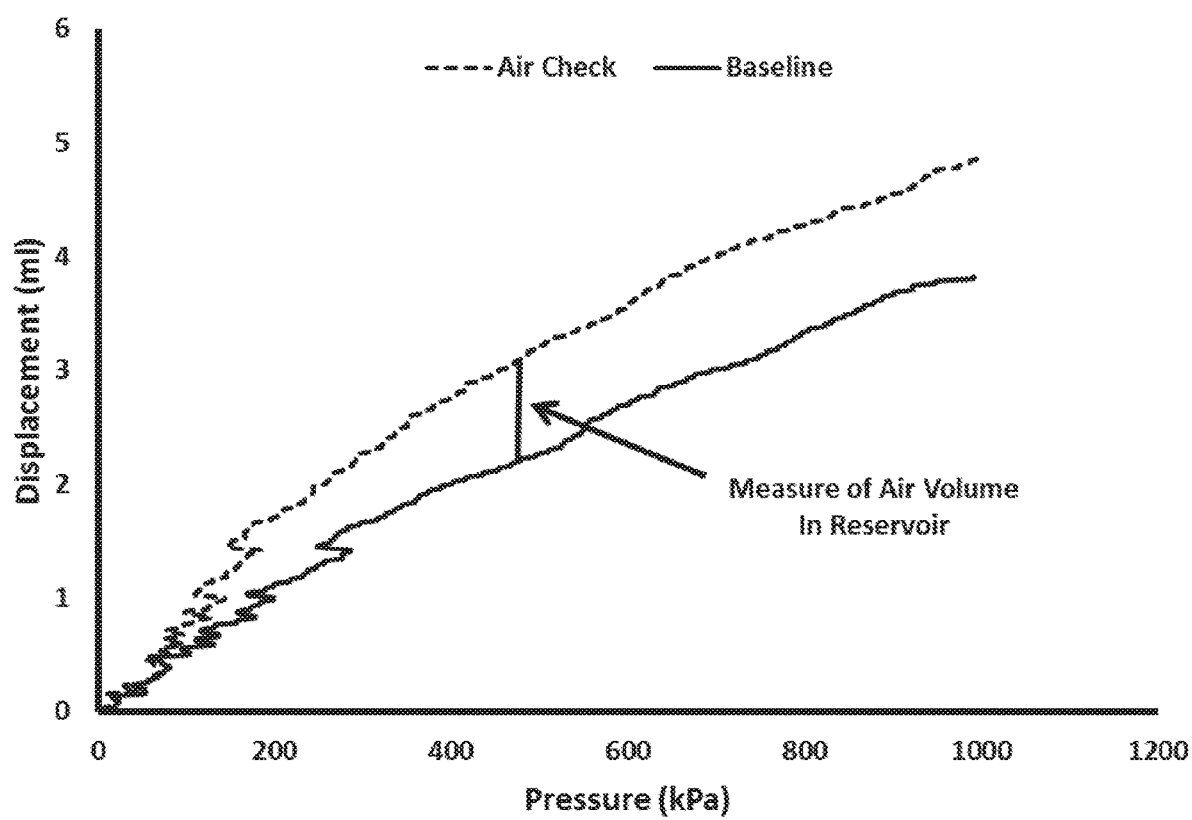
FIG. 4F is a graphical illustration of baseline compressibility data and air check compressibility data obtained during the air check protocol of the present disclosure.
Figure 5:
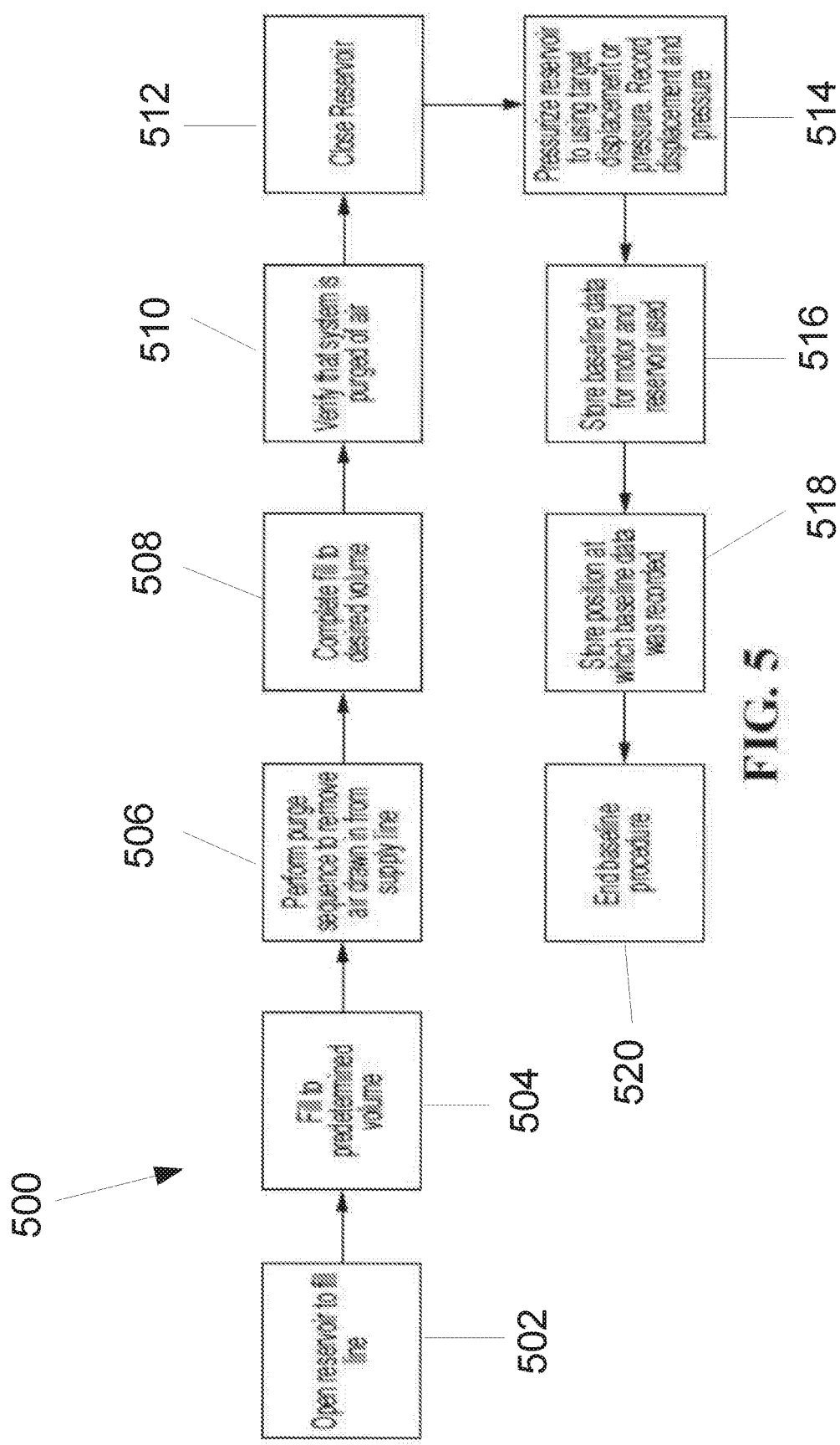
FIG. 5 is a schematic illustration of the baseline compressibility data sequence of the air check protocol.
Figure 6:
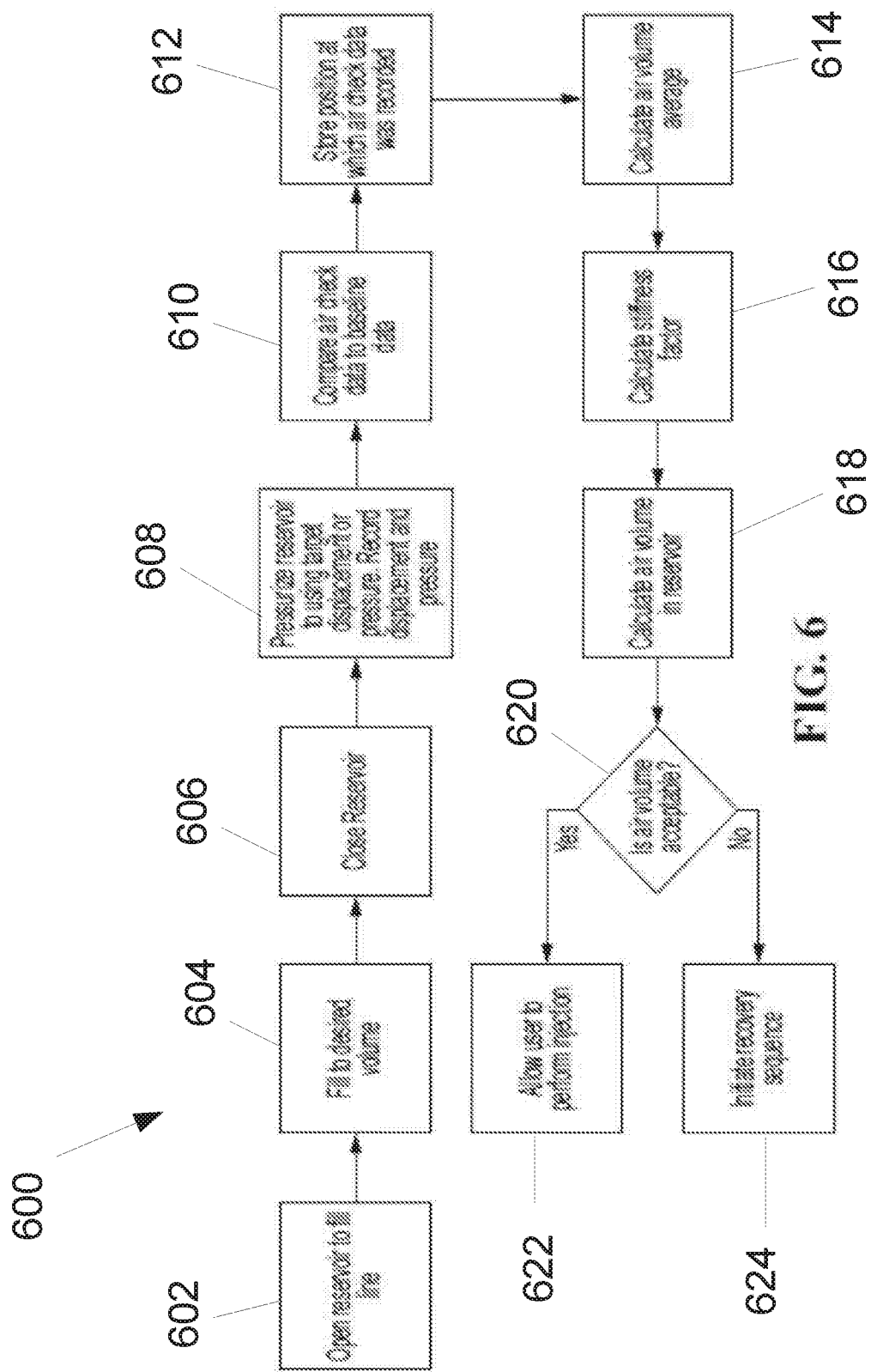
FIG. 6 is a schematic illustration of the air check compressibility data sequence of the air check protocol.
Figure 7:
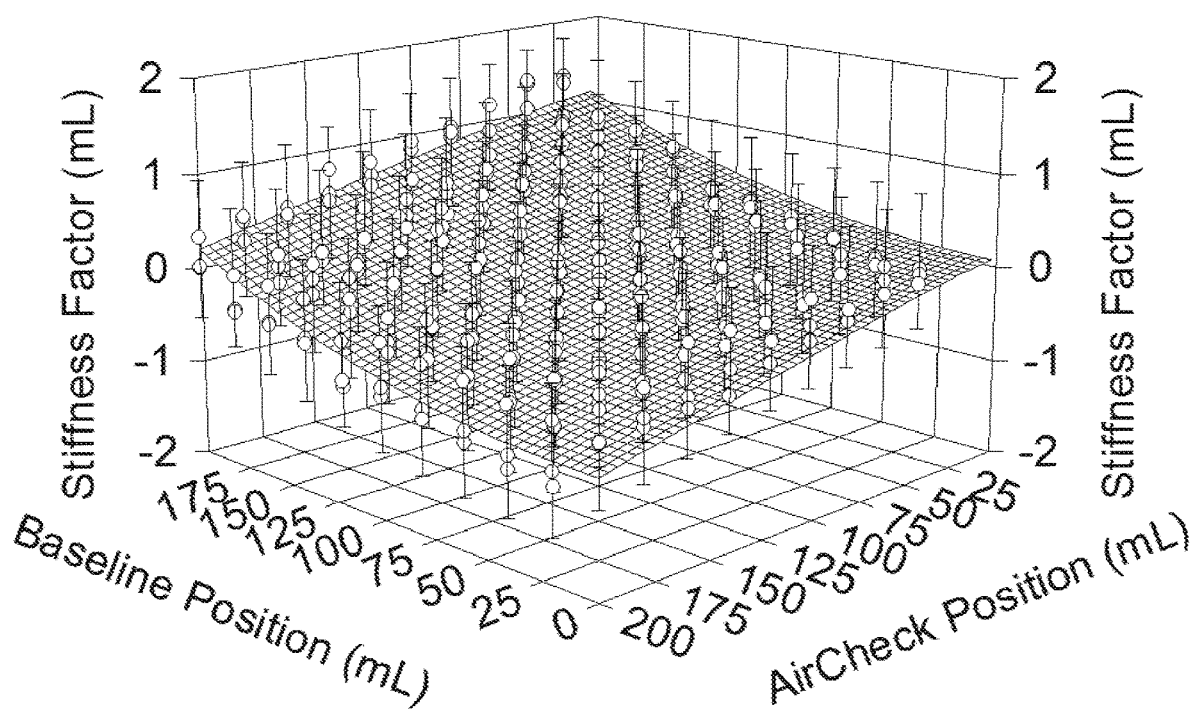
FIG. 7 is a graphical illustration of the correction factor used with the air check protocol of the present disclosure.

With reference to FIGS. 4A-7, methods and programs for detection of air within the fluid reservoir according and initiated by the electronic control devices according to various embodiments is described in detail. Non-limiting examples of sequences of various particular methods 500, 600 are illustrated in FIGS. 5 and 6. In a first phase of the method, an initial baseline value for at least one of the syringes 132 may be determined. It is to be understood that a baseline value may be determined for one, at least two, or all of the syringes 132 that are used in the fluid injector system 100. With reference to FIG. 5, according to one example, the baseline value is determined for one syringe 132. In this initial phase, the syringes 132 are installed in the fluid injector system 100 and medical fluid from the bulk fluid source 120 may be directed into the syringe 132 for example, through a fluid path and valve fluidly connecting the bulk fluid source 120 with the syringe 132. In step 502, the valve 136 on the syringe 132, which in one example may be a stopcock, is moved to a first open position to permit the medical fluid to flow into the syringe 132 from the bulk fluid source 120. In step 504, the syringe 132 may then be filled to a predetermined volume. In one example, the syringe 132 is filled to a predetermined volume ranging from 50 milliliters to 250 milliliters. In step 506, after the syringe 132 has been filled to the predetermined volume, a purge sequence may be initiated to remove any bulk volumes of air drawn into the syringe 132 from the fluid path 134. As shown in FIG. 4A, in one example, the air is purged from the syringe 132 via a purge port on the syringe 134. In another example, the air is purged from the syringe 132 through a distal end of the syringe 132. It is to be understood that the purge sequence can be any action to remove the bulk volume of air from the syringe 132, for example, by moving a piston element in a distal direction to expel any bulk volume of air back into the bulk fluid source 120 or to expel any bulk volume of air out of the syringe 132 through a fluid path to a waste reservoir 156. There may also be situations where there is a "non-injectable" air volume that does not need to be purged and can be part of the baseline value as long as it is removed from the reservoir prior to injection of the medical fluid into the patient. As shown in FIGS. 4B and 5, in step 508, after the air has been purged from the syringe 132, the syringe 132 may be filled with additional medical fluid until the predetermined volume of medical fluid is held in the syringe 132. In step 510, the processor may verify that the system is purged of air. Alternatively, in certain embodiments where the volume of air present in the fluid reservoir is a known volume, the known amount of air may be incorporated into or accounted for by the algorithms to determine a baseline value including baseline compressibility data for the fluid reservoir or syringe, which includes data for both the volume of the first amount of the medical fluid and the known volume of air.

Once the baseline value including baseline compressibility data has been determined for a fluid reservoir or syringe, the piston element of the fluid reservoir or syringe 132 may then be moved in a distal direction to deliver at least a portion of the first amount of the medical fluid from the reservoir, including, when present, the known volume of air, from the fluid reservoir. For example, the piston element of the fluid injector may be moved in the distal direction a sufficient amount to expel the at least a portion of the first amount of medical fluid and all of the air from the reservoir and through any associated fluid paths. To ensure that all of the known volume of air has been removed from the reservoir, a detector such as an air detector, may be used. For example, an air detector associated with the fluid path may monitor the fluid flowing through the fluid path to determine when no further air is detected in the fluid path.

Figure 8:
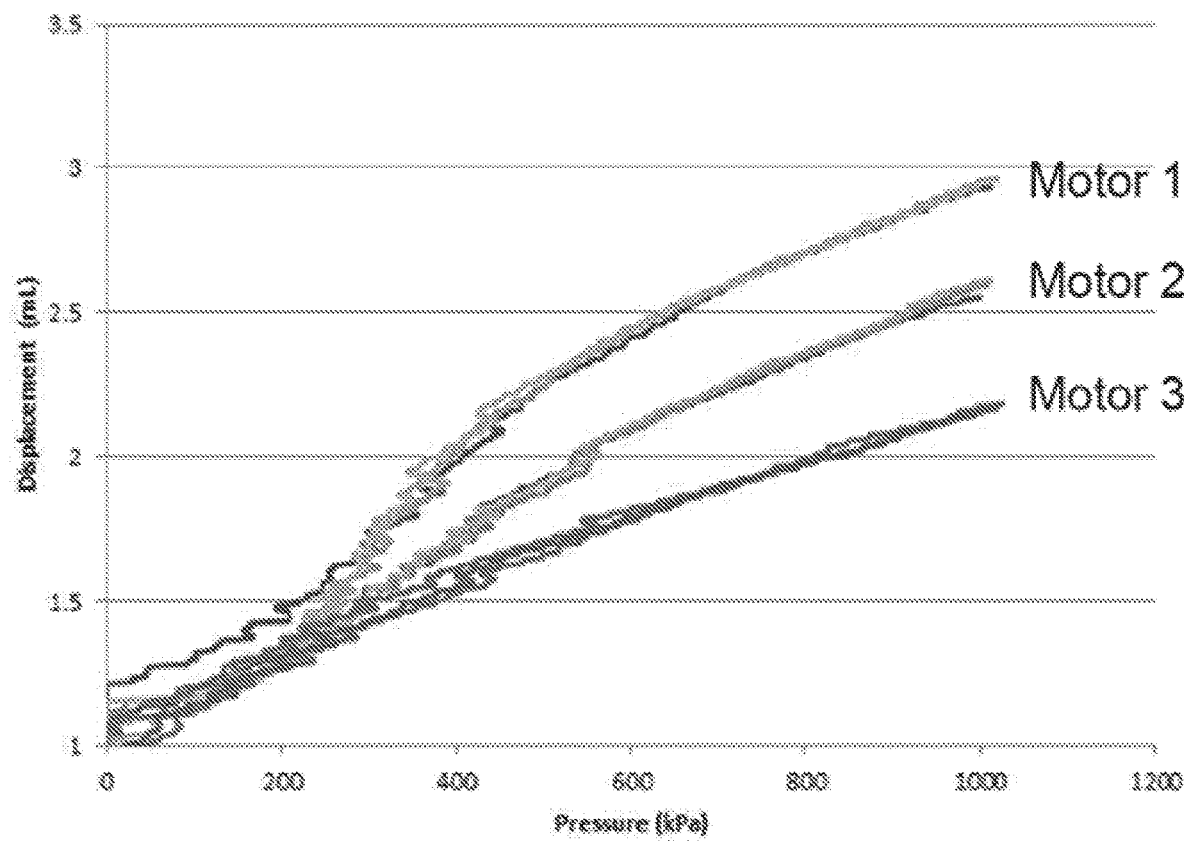
FIG. 8 is a graphical illustration of pressure versus displacement for a variety of different motors.

Describing the determination of the baseline value in greater detail, in steps 512 and 514, after the syringe 132 has been closed, the syringe 132 and any known volume of air may be pressurized until a target pressure and/or target displacement of the piston element in the syringe 132 is achieved. Pressurization is generally effected by moving the piston element associated with the fluid injector in a distal direction. In steps 516 and 518, the target pressure or target displacement may be recorded by the electronic control devices as baseline compressibility data for the syringe 132. In step 520, the baseline protocol is ended. In embodiments where the syringe reservoir contains a known volume of air along with the first amount of fluid, air compressibility data associated with the known volume is incorporated into the baseline compressibility data and accounted for in the calculation to determine the baseline value. As shown in FIG. 4C, in one example, the electronic control devices of the fluid injector system 100 may record the baseline compressibility data as pertaining to the specific syringe 132, motor, and/or piston element that was being tested. The baseline values may be specific for each motor and piston element on a fluid injector. For example, as shown in FIG. 8, the three motors and piston elements of a fluid injector according to an embodiment display different baseline compressibility curves. Further, the baseline values including baseline compressibility data for a specific motor may change over the life of the motor. According to various embodiments, to account for changes over time, the baseline values may be determined frequently, for example during the insertion of each new syringe. The electronic control devices may also record the position of the piston element at which the baseline compressibility data was recorded. Since different combinations of syringes, motors, and piston elements may have different compressibility data, the fluid injector system 100 is configured to record and store the baseline compressibility data for each combination. Further, since the combinations will have different compressibility data, the protocol for obtaining the baseline compressibility data should be initiated each time a new syringe, motor, and/or piston element is replaced in the fluid injector system 100 to ensure the most accurate baseline compressibility data is being used. The pressure value to which the syringe 132 is pressurized may be altered as desired by the user of the fluid injector system 100. In one example, the pressure value may be in the range of 5 psi to 300 psi. In a further example, the pressure value used is 1000 kPa, which ensures noise associated with the fluid injector system 100 is overcome and a linear region of stable signal is achieved. After the baseline compressibility data has been recorded, the baseline protocol is terminated by the fluid injector system 100. According to certain embodiments of the present methods, the baseline compressibility data may be acquired according to various procedures. In certain embodiments, determination or calibration may be performed at at least the following points: a) for every time a syringe or fluid path is installed into the injector; b) once for each injector system during production, and/or c) a global function can be developed to account for variation from all injector/reservoir/component combinations, for example by using a statistical assessment.

In another example of the present disclosure, the baseline compressibility data for the syringe 132 may be established using calculations or previous characterizations of properties of the fluid injector system 100, including any slack in the system 100, compliance of the components of the system 100, and/or previous baseline compressibility data measured for the system 100. According to this embodiment, historical averages for disposable components, such as the syringe and/or fluid path, may be provided to the injector for the calculation of the baseline value and may be combined along with specific historical values for a particular injector motor or global historical values for a motor configuration, to provide a global average of baseline compressibility data for a specific configuration of fluid injector and disposable components, which may be used to determine a global baseline value for the fluid injector/disposable component configuration. While this approach may not be as accurate as determining the baseline value for a particular injector with a particular syringe and/or fluid path, the global values may be sufficiently accurate to allow calculation and detection of air volumes in the syringe. For example, in certain types of injection protocols, such as computed tomography, the average value may provide sufficiently accurate air detection to prevent injection of undesired volumes of air. In contrast, in other injection protocols that are more sensitive to air injection, such as angiography, accurate determination of the baseline values may be necessary to ensure substantially no air remains in the syringe and fluid path prior to injection of the medical fluid.

As shown in FIG. 4D, after the baseline compressibility data is determined for the fluid injector system 100, the fluid injector system 100 may expel at least a portion of the first volume of medical fluid and, when present, the known volume of air from the syringe 132 prior to an actual injection procedure. The fluid injector 100 may now be prepared for an actual injection procedure using a second volume of medical fluid which incorporates the methods described herein to detect if air is present in the fluid reservoir and/or fluid path prior to the actual injection. As shown in FIG. 6, in steps 602 and 604, after the expelling process, the syringe(s) 132 may be refilled with a second amount of the medical fluid from the bulk fluid source 120. As shown in FIG. 4E, after the syringe 132 has been filled to the predetermined volume of the second amount of the medical fluid, an air check protocol is initiated by the fluid injector system 100 to ensure that no air is present in the syringe 132 and/or medical fluid held in the syringe 132 according to the embodiments of the air detection methods and protocols described herein. In summary, an air check pressurization sequence is performed to gather the air check compressibility data obtained from the refilled syringe 132 having the second amount of the medical fluid and the value is compared to the baseline compressibility data to determine whether air is present and the volume of air present in the syringe 132 and/or medical fluid stored in the syringe 132. After the syringe 132 has been filled with the second volume of medical fluid, the syringe 132 is closed off. For example, the valve 134 or stopcock is closed to isolate the syringe 132. If air is determined to be present and a volume of the air is determined based on the air check protocol, the air may be removed or expelled from the reservoir as described herein.

In steps 606 and 608, after the syringe 132 has been closed, the syringe 132 may be pressurized to the target pressure and/or target displacement of the piston element in the syringe 132. According to certain embodiments, the target pressure and/or target displacement may be the same as was established during the baseline protocol. Alternatively, according to other embodiments, a different target pressure or target volume from that used during the baseline value determination may be used and a correction factor may be incorporated into the calculation to account for the difference in fluid volume or applied pressure. In step 610, the fluid injector system 100 is then configured to compare the air check compressibility data to the baseline compressibility data, for example, by using a comparison algorithm to determine the amount of air present based on a difference between the baseline compressibility data and the air check compressibility data. In step 612, the displacement and pressure of the second amount of medical fluid in the syringe 132 is then recorded by the fluid injector system 100 as the air check compressibility data for the syringe 132 at that current refill state. The position of the syringe 132 at which the air check compressibility data was recorded is stored in the fluid injector system 100. As shown in FIGS. 4F and 6, in step 614, based on the air check compressibility data and the baseline compressibility data recorded by the fluid injector system 100, an estimated air volume present in the syringe 132 is calculated using a stored algorithm stored in the fluid injector system 100. During the comparison of the air check compressibility data and the baseline compressibility data, the force required to displace and pressurize the second amount of the medical fluid and any associate air therein within the syringe 132 in the air check protocol is compared to the force required to displace and pressurize the first amount of medical fluid within the syringe 132 during the baseline protocol to determine whether there is air present in the syringe 132 and/or second amount of medical fluid. Air and other gas that may be present in the syringe 132 is significantly more compressible than the medical fluid. Therefore, in the event air is present in the syringe 132 and/or medical fluid, the displacement of the piston element in the syringe 132 will be different in the syringe 132 that is at least partially filled with air compared to the syringe of the baseline value as determined from the first amount of medical fluid and, optionally, a known amount of air. For example, to generate 30 psi of pressure in the syringe 132, the volume of air will be compressed much more than the medical fluid which will appear as an increased travel distance of the piston compared to a syringe that is completely filled with the medical fluid. When air is present in the syringe 132, the piston element will need to travel further during pre-pressurization to reach 30 psi. In the graph shown in FIG. 4F, the air present in the syringe 132 or system 100 may be determined from the difference between the baseline compressibility data line and the air check compressibility data line. According to various embodiments, the algorithm that determines the difference between the baseline compressibility data line and the air check compressibility data line may account for a known volume of air present in the first amount of medical fluid, a difference between the piston position and/or volume of fluid in the syringe for the first amount of fluid and the second amount of fluid, and a difference between the pressure applied during the determination of the baseline compressibility data line and the air check compressibility data line.

According to embodiments, a downstream air detector 153 can be used in order to train the reservoir air detection algorithm. For example, after a fill procedure is complete, the reservoir may be pressurized in order to obtain some compressibility data as described herein. Fluid delivery from the reservoir may be monitored by the downstream air detector 153 to provide a measure of the volume air in the fluid during subsequent fluid delivery movements, where the volumes of air detected during delivery through the fluid path by the downstream air detector 153 provides correlation with the resolution or accuracy relative to the reservoir pressurization method. After completion of fluid delivery movement, the volume of air measured by reservoir pressurization methods described herein may be compared to the volume measured by the downstream air detector 153. Based on the difference in measurements obtained by the two methods, an equation or correction factor for the reservoir pressurization method may be determined and incorporated into future measurements in order to improve the accuracy of the air detection methods according to the present disclosure.

Using this approach, it is expected that the system will become less reliant on the downstream air detector 153 as more measurements are obtained, which will lead to the pressurization method developing increased accuracy over time using a real-time feedback loop of data to improve the correlation between the air check compressibility data and the volume of air present in the syringe. As such according to this embodiment, air detection prior to initiating fluid delivery to a patient may become more reliable over time. According to certain embodiments, real-time training of the pressurization algorithm may occur during manufacturing or initial testing of an individual fluid injector system 100 in order to tune air detection for a specific injector. Additionally, training of the algorithm may occur throughout at least a portion of the entire product life in such that the air detection algorithm may adapt to any changes in system behavior over time.

In step 620, after the air volume in the syringe 132 is determined by the fluid injector system 100, the determined air volume is compared to a threshold air volume value to determine whether the fluid injector system 100 can initiate the fluid injection protocol. If the determined volume of air present in the syringe is greater than the threshold air volume, an alert may be triggered to alert the user to undesired air in the syringe and the injection protocol may be halted. Alternatively, the processor may determine that a fault condition is present, for example is air volumes greater than the threshold volume are repeatedly encountered and the processor may alert the user that service of the injector may be required. In one non-limiting example, the threshold air volume value may be 1 milliliter, although larger or smaller volumes of air may be used as a threshold volume depending on the type of injection (e.g., angiography, MRI, or computed tomography). It is also considered that alternative threshold air volume values may be used by the fluid injector system 100 in the event a different procedure is being initiated by the fluid injector system 100. In the event the volume of air present in the syringe 132 and/or medical fluid is less than the threshold air volume value, the processor may permit the fluid injector system 100 to initiate the fluid injection procedure since the volume of air present in the syringe 132 and/or medical fluid is at an acceptable level.

In step 622, in the event the volume of air present in the syringe 132 and/or medical fluid is less than the threshold air volume value, the fluid injector system 100 is permitted to initiate the injection procedure for the patient. In step 624, in the event the volume of air present in the syringe 132 and/or medical fluid is greater than the threshold air volume value, the fluid injector system 100 may be prevented from initiating the fluid injection procedure since the volume of air present in the syringe 132 and/or medical fluid is too great to continue with the injection procedure. In one example, the fluid injector system 100 may issue a warning signal, for example, at least one of an audible indicator, a visual indicator, or a tactile indicator, to indicate to the user that the fluid injection procedure has been prevented due to unacceptable volumes of air present in the syringe 132 and/or the medical fluid. In certain embodiments, when an unacceptable volume of air is present in the syringe 132 and/or the medical fluid, the fluid injector system 100 may automatically initiate a priming or purging sequence to remove the air from the fluid injector system 100, or the fluid injector system 100 may indicate to the user that the priming or purging sequence must be selected and initiated by the user before the fluid injection procedure can be initiated. The priming or purging sequence may require the least amount of prime volume (waste) required to remove the air from the system, thereby ensuring air removal while minimizing the amount of waste fluid generated during the priming or purging sequence. After the priming or purging sequence is completed, the processor may draw an amount of fluid into the syringe from a bulk fluid container and repeat the air detection protocol to ensure that any air remaining in the syringe is less than the threshold volume before proceeding with the injection procedure.

Once the air volumes are calculated, specific system actions may be automatically initiated by a processor associated with the fluid injector system 100 and/or certain user actions may be restricted depending on the volume of air that has been detected by the protocol. For example, if the air volume value represents an undesired volume of air in the reservoir then injection of fluid into a patient may be disabled until the fluid injector system 100 is primed and the air is removed from the reservoir and fluid path. In addition, the calculated value may be used to efficiently remove the measured air volume from the fluid path. For example, if 2 mL of air is detected in a fluid injection system 100 where the fluid line requires 10 mL to effectively prime the fluid path, the fluid injector system 100 may adjust the prime volume to deliver at least 12 mL, or slightly more, from the reservoir to ensure the air is removed using the least amount of fluid possible. The threshold value used to drive subsequent system actions in response to air measurement may be a static value or it may be adjustable based on user preference, patient history or pre-existing condition, or vasculature access (arterial or venous). According to embodiments, the air volume measured via reservoir pressurization may be used to drive subsequent injector behaviors. For example, if the measured volume of air is greater than some threshold value, the injector may initiate or require the fluid path to be primed in order to remove the measured air volume prior to allowing a patient injection. Alternatively, if the threshold air volume is repeatedly detected, a fault condition may be indicated that requires service and correction before addition injection procedures may be performed.

After the purging sequence has been initiated and completed, the air check compressibility protocol is initiated again to determine whether any air is present in the syringe 132 and/or the medical fluid. In the event air remains in the fluid injector system 100, the purging procedure is initiated again. In the event no air is detected in the fluid injector system 100 according to the various methods herein, the fluid injection procedure may be initiated and completed to deliver medical fluid to the patient.

Figure 9:
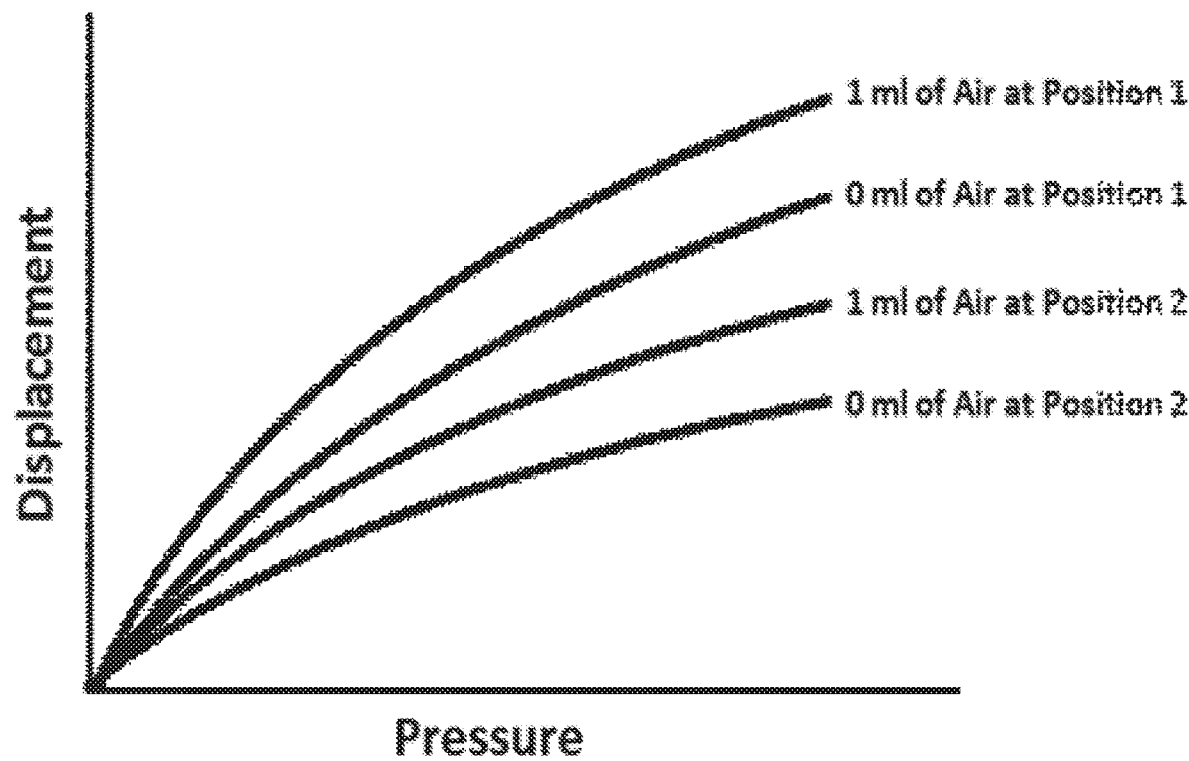
FIG. 9 is a graphical illustration of pressure versus displacement values taken at different positions.

While direct comparison of the baseline compressibility data and the air check compressibility data is correlated to a volume of air in the system, measurement errors may arise due to differences in the system state when the baseline compressibility data was recorded and the system state when the air check compressibility data was recorded. For example, the volume of the reservoir in the syringe 132 may differ when the compressibility data measurements are recorded (e.g., due to different positions of the piston element between the baseline value determination and the air check value determination), which would impact the compressibility factor of the system. For instance, the baseline compressibility data for the system may have been recorded when 200 mL of fluid was present in the syringe 132, but the air check compressibility data for the system may be recorded when only 100 mL of fluid is present in the syringe 132. Due to the difference in volume of fluid in the syringe at the two measurements, the syringe will have different compliance or capacitance which must be incorporated into any calculation. In a similar fashion, as shown in FIG. 9, the position of the plunger 144 in the syringe 132 may be at a first position when the baseline compressibility data is obtained, but the user may not wish to use the syringe 132 at the same plunger 144 position when obtaining the air check compressibility data. Therefore, since users may not wish to fill the syringe 132 to the same volume at which the syringe 132 was filled when the baseline compressibility data was recorded (for example, the injection procedure that the user may wish to initiate may only require a small volume of fluid, so the user may not need or wish to fill the syringe to the larger volume of fluid). Therefore, a correction factor may be required to account for differences in the system state between the baseline compressibility data recording and the air check compressibility data recording.

As indicated above, measurement errors may arise from variation in system state, system configuration, system capacitance or compliance, or manufacturing variability. Therefore, one or more correction factors may be used to adjust the measured air volume, based on characteristics specific to a system or elasticity variation of the system to provide accurate values of the air volume at the measured volume of fluid in the syringe 132. In one example, the correlation between the one or more correction factors, the baseline compressibility data values, and/or the air check compressibility data values are shown in the graph illustrated in FIG. 7. As used in FIG. 7 "stiffness factor" (otherwise referred to as a correction factor) may include any variables associated with any combination of system state, system configuration, system capacitance or compliance, or manufacturing variability. Such a correction factor may not be required for systems which perform measurements of a compressibility factor in a relatively consistent state. For instance, in embodiments, where the same motor, reservoir, reservoir volume, etc. are used consistently between compressibility data measurements, a correction factor may not be required and measurement resolution may be increased. For certain applications, such consistency between the compressibility data measurements may not be feasible. For example, the injector system may have multiple unique motors, such as two or three drive motors, and unique sets of reservoirs that may be exchanged every day. Such variation in the injector systems may require one or more calibration processes over predetermined times for optimal accuracy. In addition, various embodiments provide ease of use by the operator, such as where the test measurement may be performed with any volume of fluid in a reservoir, for example from 0 to 300 mL, since the user may be permitted to fill any volume over that range to perform an injection. To enhance usability of the injector system, the methods for air volume detection are desired over the entire range of reservoir volumes. Since the compliance of the reservoir is a function of the fluid volume in the reservoir, for example, as determined by a piston position, establishing a baseline compressibility data at one reservoir fluid volume and measuring air check compressibility data at another reservoir fluid volume may introduce variations in the air volume calculation. To correct for air measurement variations, differences in compliance resulting from differing reservoir fluid volumes can be calculated and used to adjust the measured air volume. Therefore, after the air check compressibility data has been recorded by the system, the one or more correction factors are determined and incorporated into the calculation of the air check compressibility data for comparison to the baseline compressibility data for air detection in the system. One embodiment or non-limiting example of a correction factor (z) equation is provided below:

$$\text{Correction Factor} = A + B*(\text{Baseline Compressibility Position in mL}) - C*(\text{Air Check Compressibility Position in mL})$$

where A, B, and C are variables depending on the stiffness and compliance of the specific motor and reservoir used for various baseline start volumes and air check start volumes. For specific embodiments, A may be an offset value, B may be associated with the slope along the baseline position axis of FIG. 7 and C may be associated with the slope along the air check position axis of FIG. 7. In one non-limiting example, the value of A in the equation above ranges from −5 to 5, the value of B in the equation above ranges from −30 to 30, and the value of C in the equation above ranges from −30 and 30. In one non-limiting example, the value of A in the equation above is 0.001, the value of B in the equation above is 0.009, and the value of C in the equation above is 14.611. It is to be understood, however, that the values of A, B, and C will change depending on the specific fluid injector system and system components that are being used. Values for A, B, and C may be stored in the memory of an injector or otherwise available for specific baseline and air check volumes in one or more "look-up" tables listing values for the variables. While the correction factor equation is shown as linear, other embodiments may include non-linear equations, depending on the fit of the associated surface plot for the stiffness factor against the baseline start volume and the air check start volume.

The present air detection method according to various embodiments herein provides various benefits to the fluid injector system 100. In particular, the air measurement in the fluid occurs prior to injection of the fluid into a patient. This method minimizes any risk of air injection into the patient as the injection procedure may be halted prior to injection initiation if air volumes greater than a threshold volume are detected. In contrast, many conventional methods require a sensor, such as an air detector, to sense air while it passes through the patient line to the patient and it may be difficult to stop the injection procedure in time. Further, the present methods may result in less wasted medical fluid since air presence may be determined and purged prior to an injection. Further, benefits include increased efficiency of injection procedures since the procedures need not be halted in the middle and the fluid injection protocol reset to the beginning. The described methods also proactively work to prevent air injection, allowing confidence that only non-harmful volumes of air are present in the system and reduces the need to interrupt medical injection procedures, thereby reducing patient inconvenience and medical fluid waste. The present methods also benefit from reduced lag in response time. Conventional methods may be impacted by measurement of a dynamic fluid path, for example where the air is detected and measured after it has passed the sensor. The present method measurements are also not dependent on fluid path impedance, fluid properties, or fluid dynamics (e.g., flow rate, interaction between air and fluid, etc.). The disclosed methods provide stability and scalability and the air detection is not dependent on fluid path features, such as length and components.

The methods according to various embodiments also allow for a baseline measurement to be calculated or determined for every possible disposable/hardware combination and configuration and can correct for mechanical slack associated with the various combinations and injector components, including increase in slack that may occur due to mechanical component wear over time. This allows for optimization of air detection accuracy for each disposable used. In addition, the methods substantially eliminate potential inaccuracies introduced during injector or disposable manufacturing. The described methods may be applied to closed fluid reservoir systems, which can account for compliance issues and provide improved accuracy in fluid injections. It is also contemplated that the methods and protocols described above may be used in an open system, which accounts for fluid flow while making the baseline and air check compressibility measurements. The various methods may be automated for an automated injection procedure or protocols. Automation may minimize the possibility of user error during injection protocols, thereby providing increased patient safety. The disclosed methods may also be used to optimize the volume required for priming air from the system. For example, by having a value for the air trapped within the system, the system may be primed for a time and a prime volume that minimizes fluid waste. Various embodiments of the present methods may be used for any closed system, such as CT, CV, infusion injection, etc. that include a valve that can be used to close the system and fluidly isolate the fluid reservoir.

While various examples of the present disclosure were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. An injector system for delivering a medical fluid, comprising:
   at least one syringe defining a reservoir operatively connected to a piston, the at least one syringe comprising a plunger and at least one port in fluid communication with the reservoir, the reservoir configured to contain the medical fluid; and
   at least one processor programmed or configured to:
     based on an air check protocol for detecting air in the reservoir, determine a baseline value comprising baseline compressibility data for the at least one syringe of the injector system, wherein the reservoir is substantially filled with a first amount of the medical fluid and a known volume of air;
     deliver the first amount of the medical fluid from the reservoir;
     refill the reservoir with a second amount of the medical fluid;
     based on the air check protocol, perform an air check pressurization sequence by gathering air check compressibility data for the at least one syringe of the injector system; and
     based on the air check protocol, compare the air check compressibility data with the baseline compressibility data to determine a volume of air present in the reservoir
   wherein the processor is further programmed or configured to, based on the air check protocol, incorporate a correction factor when comparing the air check compressibility data with the baseline compressibility data to account for variations in at least one of deflection of one or more injector system components, different volumes of the medical fluid compared to the volume of the first amount of the medical fluid used for determining the baseline compressibility data, and different positions of the piston compared to a position of the piston when determining the baseline compressibility data.

2. The injector system of claim 1, wherein the baseline value is determined to account for a deflection of one or more components of the injector system and compliance of the reservoir and a fluid path, and a compressibility of the known volume of air.

3. The injector system of claim 1, wherein the processor is further programmed or configured to, based on the air check protocol, purge any air in the first amount of the medical fluid from the reservoir before determining the baseline value.

4. The injector system of claim 1, wherein the processor is further programmed or configured to, based on the air check protocol, deliver a prime volume of the second amount of the medical fluid from the reservoir, wherein the prime volume of the second amount of the medical fluid has a volume greater than the volume of air present in the reservoir.

5. The injector system of claim 4, wherein the further programming or configuring the processor to deliver the prime volume of the second amount of the medical fluid further comprises optimizing the prime volume equal to a minimum volume of the second amount of the medical fluid necessary to remove the volume of air present in the reservoir.

6. The injector system of claim 4, further comprising a downstream air detector, wherein the downstream air detector is programmed or configured to confirm that no further air is present in a fluid path after the prime volume of the second amount of medical fluid as it is delivered from the reservoir.

7. The injector system of claim 1, wherein the processor is further programmed or configured to, based on the air check protocol, determine whether the volume of air present in the reservoir exceeds a predetermined volume value.

8. The injector system of claim 7, wherein, in the event the volume of air in the reservoir exceeds the predetermined volume value, the processor is further programmed or configured to, based on the air check protocol, purge the volume of air from the reservoir before the second amount of the medical fluid is delivered from the reservoir or determine whether a fault condition exists.

9. The injector system of claim 8, wherein, after the volume of air has been purged from the reservoir, the processor is further programmed or configured to, based on the air check protocol, perform an additional air check pressurization sequence by gathering additional air check compressibility data from the reservoir, and compare the additional air check compressibility data with the baseline compressibility data to determine whether any air remains in the reservoir.

10. The injector system of claim 7, wherein the predetermined volume value ranges from 0.1 milliliters to 20 milliliters.

11. The injector system of claim 1, wherein comparing the air check compressibility data with the baseline compressibility data to determine the volume of air present in the reservoir comprises using an embedded algorithm to compare the air check compressibility data with the baseline compressibility data to determine the volume of air present in the reservoir.

12. The injector system of claim 1, wherein the at least one syringe further includes at least one valve associated with the at least one port, the at least one valve is configured to move between a fill position, a delivery position, and a closed position in response to one or more instruction from the at least one processor.

13. The injector system of claim 12, wherein the at least one valve is in the closed position for at least one of determining the baseline compressibility data and performing the air check pressurization sequence.

14. A method for detecting air in at least one reservoir of a fluid injector system, the method comprising:
    determining a baseline value comprising baseline compressibility data for the at least one reservoir of the fluid injector system, the at least one reservoir having at least one port, wherein the at least one reservoir is substantially filled with a first amount of a medical fluid and a known amount of air;
    delivering the first amount of the medical fluid from the at least one reservoir;
    refilling the at least one reservoir with a second amount of the medical fluid;
    performing an air check pressurization sequence comprising pressurizing the medical fluid in the at least one reservoir and gathering air check compressibility data;
    comparing the air check compressibility data with the baseline compressibility data to determine a volume of air present in the at least one reservoir; and
    incorporating a correction factor when comparing the air check compressibility data with the baseline compressibility data to account for variations in at least one of deflection of one or more fluid injector system components, different volumes of the medical fluid compared to the volume of the first amount of the medical fluid used for determining the baseline compressibility data, and different positions of a piston in the fluid injector system compared to a position of the piston when determining the baseline compressibility data.

15. The method of claim 14, wherein determining the baseline value comprises accounting for a deflection of the fluid injection system, compliance of the at least one reservoir and a fluid path, and a compressibility of the known volume of air.

16. The method of claim 14, further comprising purging the known volume of air from the at least one reservoir prior to determining the baseline value.

17. The method of claim 14, further comprising delivering a prime volume of the second amount of the medical fluid from the at least one reservoir, wherein the prime volume of the second amount of the medical fluid has a volume greater than the volume of the air present in the at least one reservoir.

18. The method of claim 17, wherein delivering the prime volume of the second amount of the medical fluid further comprises optimizing the prime volume to equal to a minimum volume of the second amount of the medical fluid necessary to remove the volume of the air present in the at least one reservoir.

19. The method of claim 14, further comprising determining whether a fault condition exists when the volume of air present in the at least one reservoir exceeds a predetermined volume value.

20. The method of claim 14, further comprising closing a fluid path associated with the at least one port of the at least one reservoir prior to at least one of determining the baseline value and performing the air check pressurization sequence.

21. The method of claim 14, wherein the second amount of the medical fluid is different than the first amount of the medical fluid.

* * * * *

UNITED STATES PATENT AND TRADEMARK OFFICE
CERTIFICATE OF CORRECTION

PATENT NO. : 12,251,544 B2
APPLICATION NO. : 17/048219
DATED : March 18, 2025
INVENTOR(S) : McDermott et al.

Page 1 of 1

It is certified that error appears in the above-identified patent and that said Letters Patent is hereby corrected as shown below:

In the Specification

In Column 2, Line 54, delete "positon" and insert -- position --, therefor.
In Column 4, Line 24, delete "disclsoure" and insert -- disclosure --, therefor.
In Column 5, Line 1, delete "positon" and insert -- position --, therefor.
In Column 6, Line 66, delete "use" and insert -- use with the --, therefor.
In Column 9, Line 19, delete the second occurrence of "to" and insert -- of --, therefor.
In Column 17, Line 58, delete "volume" and insert -- volume of --, therefor.
In Column 18, Line 32, delete the second occurrence of "is" and insert -- if --, therefor.
In Column 19, Line 42, delete "addition" and insert -- additional --, therefor.

In the Claims

In Column 22, Line 63, in Claim 1, delete "reservoir" and insert -- reservoir, --, therefor.

Signed and Sealed this
Tenth Day of June, 2025

Coke Morgan Stewart
*Acting Director of the United States Patent and Trademark Office*